(12) United States Patent
Alghamdi

(10) Patent No.: US 9,447,119 B2
(45) Date of Patent: Sep. 20, 2016

(54) CHEMICAL COMPOUND FOR INHIBITING THE GROWTH AND PROLIFERATION OF HUMAN LIVER CANCER CELLS HEPG2 AND METHOD FOR SYNTHESIZING IT

(71) Applicant: Zainab Saeed Alghamdi, Dhahran (SA)

(72) Inventor: Zainab Saeed Alghamdi, Dhahran (SA)

( * ) Notice: Subject to any disclaimer, the term of this patent is extended or adjusted under 35 U.S.C. 154(b) by 0 days.

(21) Appl. No.: 14/593,683

(22) Filed: Jan. 9, 2015

(65) Prior Publication Data

US 2016/0200740 A1 Jul. 14, 2016

(51) Int. Cl.
*C07D 513/14* (2006.01)
*C07D 333/80* (2006.01)

(52) U.S. Cl.
CPC ........... *C07D 513/14* (2013.01); *C07D 333/80* (2013.01)

(58) Field of Classification Search
CPC .......................... C07D 513/14; C07D 333/80
See application file for complete search history.

(56) References Cited

PUBLICATIONS

Prasad, M.R.,Microwave Assisted Synthesis of Some Novel Thiadiazolothienopyrimidines. ChemInform 2007, R0515, 37-149, p. 1.*

* cited by examiner

*Primary Examiner* — Samantha Shterengarts
*Assistant Examiner* — Matt Mauro
(74) *Attorney, Agent, or Firm* — Dennis H. Lambert

(57) ABSTRACT

The compound "2-((4-nitrophenyl)amino)-7,8,9,10-tetrahydro cyclohepta[4,5]thieno[2,3-d][1,3,4]thiadiazolo[3,2-a]pyrimidin-11(6H)-one" and method of synthesizing it, wherein the compound is effective to inhibit the growth and proliferation of human liver cancer cells HepG2. The compound has a higher efficiency to inhibit the growth and proliferation of these cells as it has an inhibitory concentration value ($IC_{50}$) of 0.7 μg, compared to reference medication Doxorubicin that has an ($IC_{50}$) value of 1.2 μg. It further surpasses that reference medication at all tested concentrations. The method includes the steps of: preparing a first compound of cycloheptanone, ethylcyanoacetate, sulfur, ethanol and diethylamine; preparing a second compound by heating of the first compound with excess of hydrazine hydrate in absolute ethanol as solvent; preparing a third compound by heating the second compound with carbon disulphide in dry pyridine; and preparing the compound of the invention by reacting the third compound with 4-nitrophenylisothiocyanate in dry N,N-methylformamide as solvent.

32 Claims, 15 Drawing Sheets

US 9,447,119 B2

CHEMICAL COMPOUND FOR INHIBITING THE GROWTH AND PROLIFERATION OF HUMAN LIVER CANCER CELLS HEPG2 AND METHOD FOR SYNTHESIZING IT

TECHNICAL FIELD

This invention relates to chemical compounds useful in the treatment of diseases, and particularly to a new compound for the treatment of human liver cancer and to a method for synthesizing the compound.

BACKGROUND ART

There are more than 200 types of cancer, each with different causes, symptoms and treatments. Cancer is among the leading causes of morbidity and mortality worldwide. There were approximately 14.1 million new cases and 8.2 million cancer related deaths in 2012, with incidence rates varying across the world.

Cancer is the second leading cause of death in the United States, exceeded only by heart disease. In the United States in 2014, nearly 586,000 people are expected to die of cancer and more than 1.66 million new cancer cases are expected to be diagnosed.

The financial costs of cancer also are overwhelming According to the National Institutes of Health, cancer costs the United States an estimated $263.8 billion in medical costs and lost productivity in 2010, but the cost of cancer extends beyond the number of lives lost and new diagnoses each year. Cancer survivors, as well as their family members, friends, and caregivers, may face physical, emotional, social, and spiritual challenges as a result of their cancer diagnosis and treatment.

Hepatocellular carcinoma is one of the most lethal human cancers because of its high incidence and its metastatic potential, and it is among the most resistant to treatment. It is the third leading cause of cancer-related deaths worldwide.

Substantial research has been conducted worldwide, with limited success, in an effort to find effective treatments and/or a cure for cancer. The examples below describe some of those efforts, although the article in *Molecules* by M. Ismail, et al relates to the treatment of Alzheimer's disease, and the article by M. Raghuprasad, et al in the *Asian Journal of Chemistry* and the article by B. V. Ashalatha, et al in the *European Journal of Medicinal Chemistry* both relate to antimicrobial activity.

In a research paper by Rafat Mohareb and Abdelgawad Fahmy, titled *Cytotoxicity of Novel 4,5,6,7-Tetrahydrobenzo [b]thiophene Derivatives and Their Uses As Anti-Leishmanial Agents*, published in the European Chemical Bulletin, 2013, 2(8), 545-553, the authors studied the cytotoxicity of 4,5,6,7-tetrahydrobenzo[b]thiophene derivatives in the treatment of breast adenocarcinoma, non-small-cell lung cancer, and central nervous system lymphoma (CNS lymphoma). The compounds proposed by Mohareb and Fahmy all have a thiophene ring attached to the cyclohexene ring. The chemical structure is depicted in FIG. 1.

In a paper by Dhilli Gorja, Shiva Kumar, K. Mukkanti, and Manojit Pal, titled *C—C(alkynylation) vs C—O(ether) Bond Formation Under Pd/C—Cu Catalysis; Synthesis and Pharmacological Evaluation of 4-Alkynylthieno[2,3-d]pyrimidines*, published in the Journal of Organic Chemistry 2011, 7, 338-345, the authors proposed alkynyl substituted thienopyrimidines, notably 6-ethynylthieno[3,2-d] and 6-ethynylthieno[2,3-d]pyrimidin-4-aniline derivatives useful in the treatment of leukemia. The authors used a Pd/C-CuI-PPh$_3$ catalytic system to facilitate C—C bond formation between 4-chlorothieno[2,3-d]pyrimidines and terminal alkynes in methanol. A variety of 4-alkynylthieno[2,3-d] pyrimidines were prepared via alkynylation of 4-chlorothiene[2,3-d]pyrimidines. The chemical structure is depicted in FIG. 2.

In an article titled *Synthesis and Biological Evaluation of Thiophene Derivatives As Acetylcholinesterase Inhibors*, published in Molecules 2012, 17, 7217-7231, Mohamed Ismail, Mona Kamel, Lamia Mohamed, Samar Faggal and Mai Galal proposed thiophene derivatives as acetylcholinesterase inhibitors useful in the treatment of Alzheimer's disease. The chemical structure is depicted in FIG. 3.

M. Raghuprasad, S. Mohan, B. Das and S. Srivastava published in the Asian Journal of Chemistry 2007; 19(5): 2813-7, a paper titled *Synthesis and Antimicrobial Activity of Some Thiadiazolo Thienopyrimidines*, in which thiadiazolo thienopyrimidin derivatives are attached with cyclohexene ring and the benzene ring is attached with methoxy group (—OCH$_3$), but do not have a carbonyl group (C═O) nor is a benzene ring attached with a nitro group (—NO$_2$). The biological objective in their paper was antimicrobial activity. The chemical structure is depicted in FIG. 4.

B. V. Ashalatha, B. Narayana, K. K Raj Vijaya and S. Kumari published in the European Journal of Medicinal Chemistry 2007, 42, 719-728, a paper titled *Synthesis of Some New Bioactive 3-amino-2-mercabto-5,6,7,8-tetrahydro[1]benzothieno[2,3-d]pyrimidin-4-one Derivatives*, in which their compounds have thiadiazolo thienopyrimidin derivatives attached with cyclohexene ring. The compound is not attached with a cycloheptene ring. Their biological objective was antimicrobial, anti-inflammatory, anticonvulsant and neuropsychobehavioural effects. The chemical structure is depicted in FIG. 5.

V. Alagarsamy, U. S. Pathak, V. Rajasolomon, S. Meena, K. V. Ramseshu, and R. Rajesh published in the Indian Journal of Heterocyclic Chemistry 2004; 13; 347. 2004; 13; 347 an article titled *Anticancer, Antibacterial and Antifungal Activities Of Some 2-substituted(1,3,4)thiadiazolo(2,3-b)tetrahydrobenzo(b)thieno(3,2-e)pyrimidines*, wherein they synthesized (1,3,4)thiadiazole(2,3-b)tetrahydro-benzothieno [3,2-e]pyrimidines and then screened them for anticancer, antibacterial and antifungal activities. Their compounds have thiadiazolo thienopyrimidin derivatives attached with cyclohexene ring. The compound is not attached with cycloheptene ring. Their objectives are anticancer, antibacterial and antifungal. The chemical structure is depicted in FIG. 6.

Drugs have been developed that produce favorable results in some cancers that are more susceptible to treatment, but no really effective drug has been developed for the treatment of hepatocellular carcinoma. The compounds mentioned in the articles noted above have limited, if any, effectiveness in the treatment of liver cancer.

Accordingly, there is a need for a treatment that is effective in reducing the growth and propagation of human liver cancer cells (HepG2).

SUMMARY OF THE INVENTION

Applicant has synthesized a new chemical compound for reducing the growth and propagation of human liver cancer cells (HepG2). The compound was tested on human liver cancer cells for effectiveness at various degrees of concentration.

The test results revealed that the new compound has a higher efficiency to inhibit the growth and proliferation of these cells as it has an inhibition concentration value ($IC_{50}$) of 0.7 μg compared to the reference medication (Doxorubicin) that has an inhibition concentration value of 1.2 μg. Not only do the test results confirm the high efficiency of the compound of the invention but also the potential therapeutic benefit from using it.

The chemical compound of the invention is synthesized by:
1) first preparing a compound I (founding compound) according to Gewald;
2) second, preparing a compound II (carboxylic acid hydrazide) by mainly utilizing carboxylic acid ester with hydrazine or hydrazine derivatives in ethanol and reacting it with compound I;
3) third, preparing a compound III by heating compound II with carbon disulphide in dry pyridine on water-bath or ultrasonic sound; and
4) finally, preparing the compound of the invention by reacting compound III with 4-nitrophenylisothiocyanate in dry dimethylformamide (DMF) as solvent.

All compounds were characterized by using different spectrum means such as infrared, nuclear magnetic resonance for protons and finally mass spectrum.

The effectiveness of the compound of the invention, "2-((4-Nitrophenyl)amino)-7,8,9,10-tetrahydrocyclohepta[4,5]thieno[2,3-d][1,3,4]thiadiazolo[3,2-a]pyrimidin-11(6H)-one", was tested on human liver cancer cells HepG2 by using isolated-biopsy cells from males with an average age of about 15 years. The new compound was found to have a higher efficiency to inhibit the growth and proliferation of these cells as it has an inhibition concentration value of ($IC_{50}$) of 0.7 μg which surpasses, at all tested concentrations, the reference medication (Doxorubicin) that has an inhibition concentration value of 1.2 μg.

As shown by applicant's discovery, the invention compound is medically effective as a new treatment for human liver cancer.

BRIEF DESCRIPTION OF THE DRAWINGS

The foregoing, as well as other objects and advantages of the invention, will become apparent from the following detailed description when taken in conjunction with the accompanying drawings, wherein like reference characters designate like parts throughout the several views, and wherein.

DETAILED DESCRIPTION OF THE BEST MODES OF CARRYING OUT THE INVENTION

The chemical compound of the invention, "2-((4-Nitrophenyl)amino)-7,8,9,10-tetrahydrocyclohepta[4,5]thieno[2,3-d][1,3,4]thiadiazolo[3,2-a]pyrimidin-11(6H)-one", was prepared by the chemical reaction of "4-nitrophenylisothiocyanate" with "3-amino-2-thioxo-2,3,6,7,8,9-hexahydro-1H-cyclohepta[4,5]thieno[2,3-d]pyrimidin-4(5H)-one" (III). The latter was prepared by the reaction of "2-amino-3-carbohydrazide derivative" with carbon disulfide through a series of chemical reactions according to the scheme shown in FIG. 21. The chemical structure for the compound of the invention is shown in FIG. 22.

Figure 1:
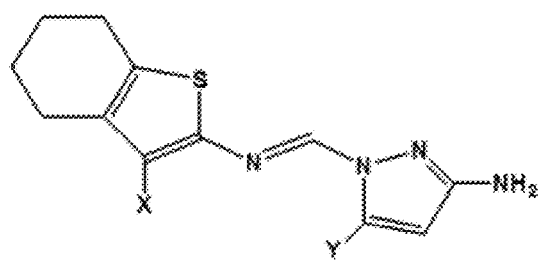
FIG. 1 shows the chemical structure of the prior art compounds proposed by Mohareb and Fahmy.
Figure 2:
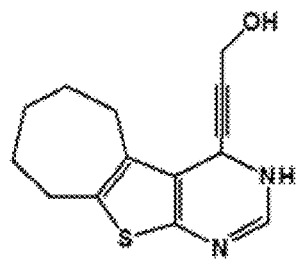
FIG. 2 shows the chemical structure of the prior art compound proposed by Gorj a, et al.
Figure 3:
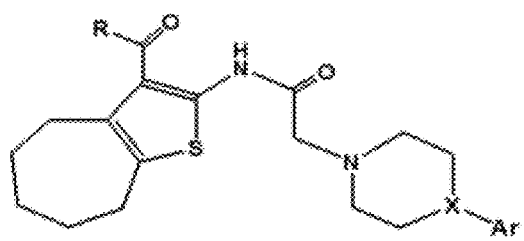
FIG. 3 shows the chemical structure of the prior art compound proposed by Ismail, et al.
Figure 4:
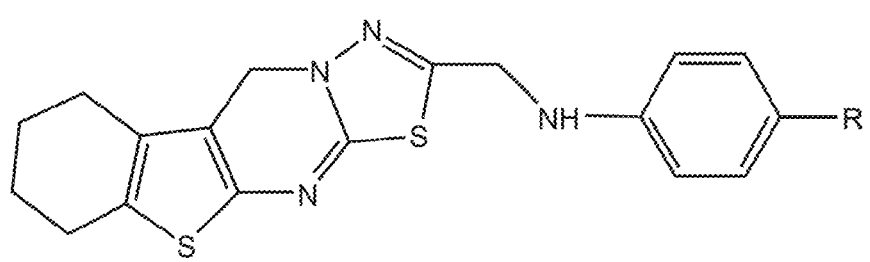
FIG. 4 shows the chemical structure of the prior art compound proposed by Raghuprasad, et al.
Figure 5:
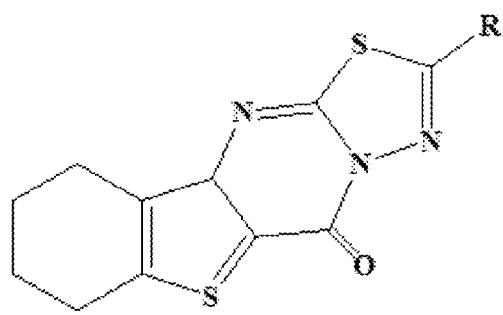
FIG. 5 shows the chemical structure of the prior art compound proposed by Ashalatha, et al.
Figure 6:
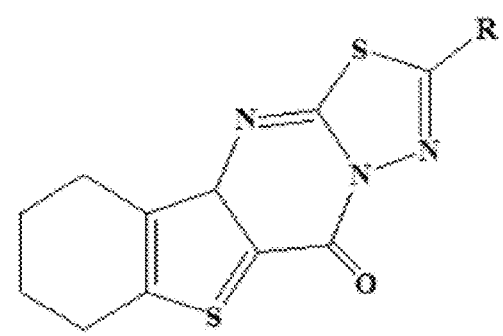
FIG. 6 shows the chemical structure of the prior art compound proposed by Alagarsamy, et al.
Figure 7:
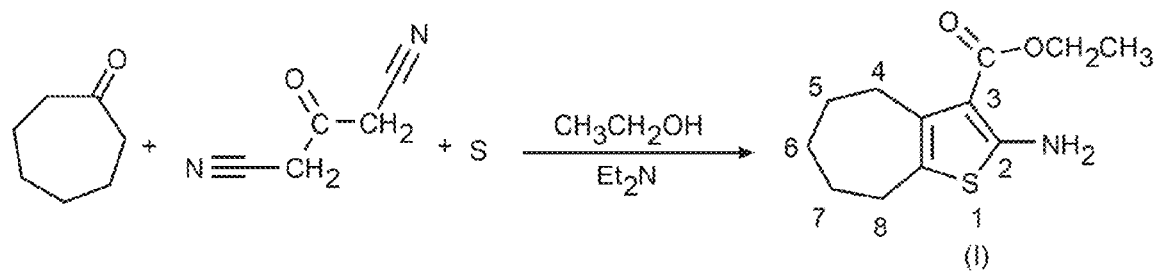
FIG. 7 shows the chemical reactions that produce the founding compound in accordance with the teachings of Gewald, and that is used in synthesizing the compound of the invention.
Figure 8:
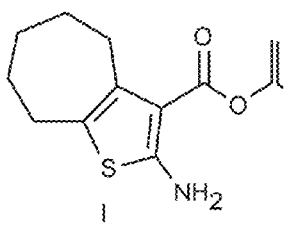
FIG. 8 shows the chemical structure of compound (I).

The founding compound, compound (I), "Ethyl-2-amino-5,6,7,8-tetrahydro-4H-cyclohepta[b]thiophene-3-carboxylate", can be prepared by a number of known conventional ways, but in the preferred method according to the present invention was prepared according to Gewald (Gewald, K., E. Schinke, and H. Böttcher, *Heterocyclen aus CH-aciden Nitrilen, VIII. 2-Amino-thiophene aus methylenaktiven Nitrilen, Carbonylverbindungen and Schwefel. Chemische Berichte*, 1966, 99(1): p. 94-100). Gewald devised the most facile and promising set of synthetic reactions leading to 2-aminothiophene with a carboxylate group in position 3. The second version of the Gewald reactions consists of a one-pot procedure that is extensively used for this synthesis. The convenient technique includes the condensation of cycloheptanone, ethyl cyanoacetate and a sulfur element in ethanol with the presence of amine as diethylamine for 24 hours at room temperature. The structure of compound (I), shown in FIG. 8, was assigned on the basis of infrared (IR), nuclear magnetic resonance ($^1$H-NMR) and mass spectrum (MS) spectral data.

In the preparation of compound (I) according to the preferred method, 0.05 mmol cycloheptanone, 0.05 mmol ethylcyanoacetate, 1.67 g sulfur and 10 ml ethanol were mixed and stirred together. To this well stirred mixture 10 ml of diethylamine was added drop wise until the sulfur dissolved and the mixture of cycloheptanone, ethylcyanoacetate, sulfur, ethanol and diethylamine was stirred on cold for overnight. The reaction mixture was cooled with 60 ml of crushed ice, the solid product (precipitate) was filtered off, dried and recrystallized by petroleum ether.

Figure 9:
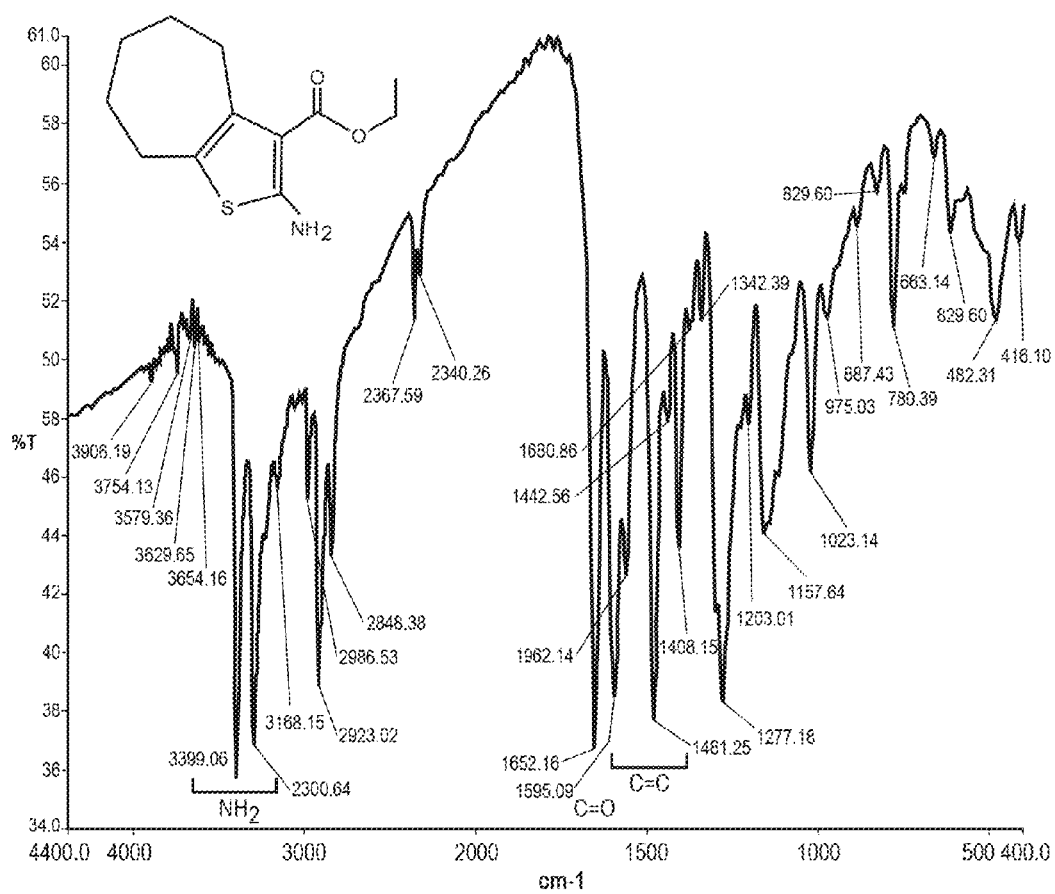
FIG. 9 depicts the Infrared spectra of compound (I).

The infrared spectra (IR) of compound (I), see FIG. 9, showed absorption peaks at 3399.06, 3300.64 cm$^{-1}$ (NH$_2$), 1652.16 cm$^{-1}$ (C=O ester), 1595.09, and 1562.14 cm$^{-1}$ (C=C).

Figure 10:
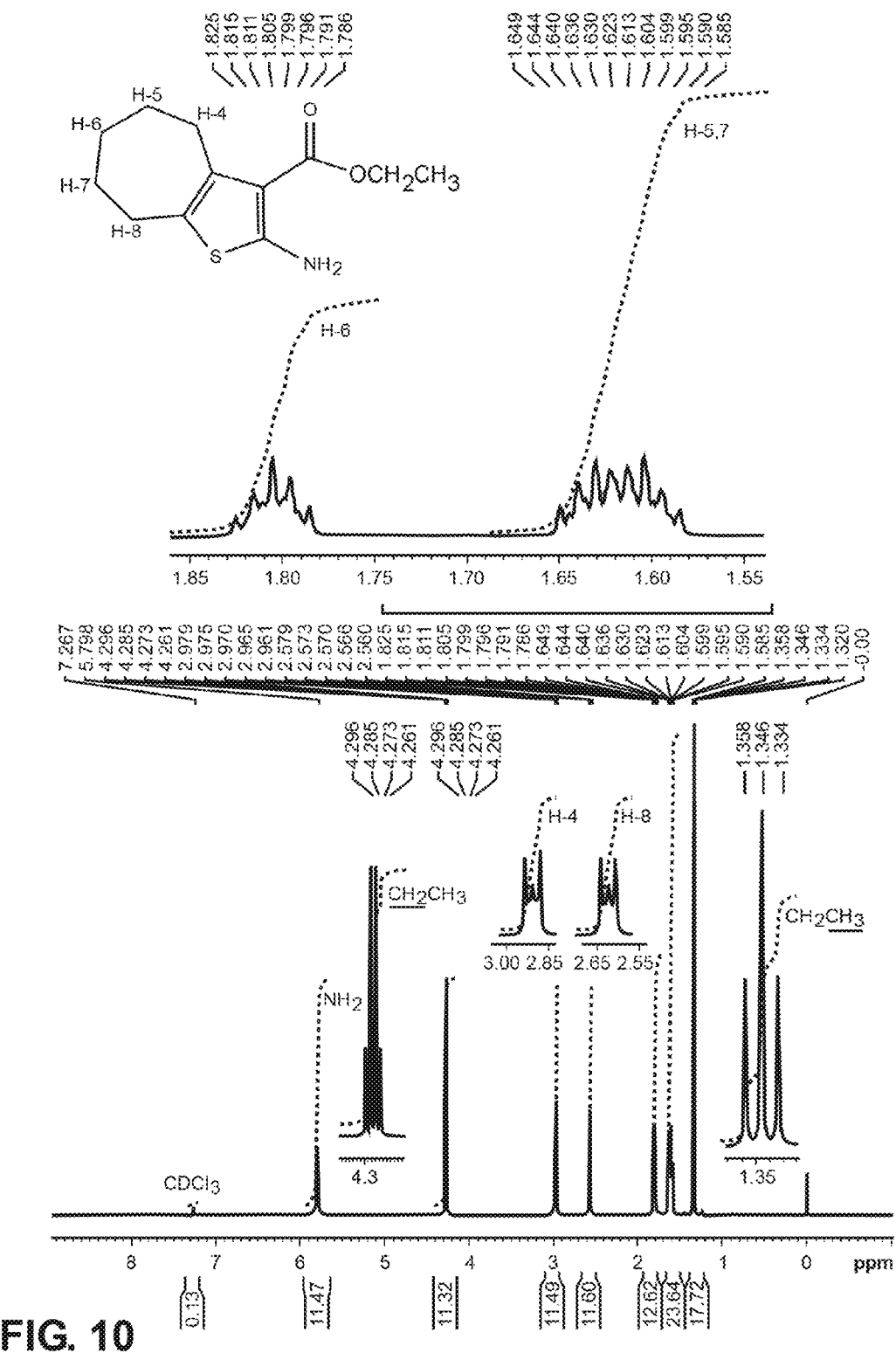
FIG. 10 depicts the nuclear magnetic resonance spectrum of the protons in compound (I).

The nuclear magnetic resonance spectra ($^1$H-NMR) of compound I, see FIG. 10, showed a triplet at δ1.35 ppm (3H, $^3$J=7.2 Hz) corresponding to the three hydrogens of CH$_3$ ester, a multiplet at δ1.59-1.65 ppm (4H, H-5,7), a multiplet at δ1.81 ppm (2H, H-6), a triplet at δ2.57 ppm (2H, $^3$J=5.4 Hz, H-8), a triplet at δ2.84 ppm (2H, $^3$J=5.4 Hz, H-4) corresponding to the methylene groups protons in the cycloheptene moiety and quartet at δ4.28 ppm corresponding to the tow hydrogens of CH$_2$ ester, while the NH$_2$ protons appeared as a single at δ5.80 ppm (2H).

Figure 11:
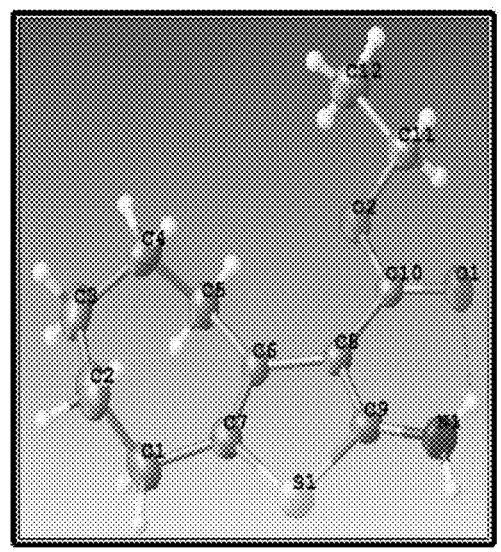
FIG. 11 depicts the X-ray spectrum of compound (I).

The X-ray for compound (I) conformed the structure. See FIG. 11.

Figure 12:
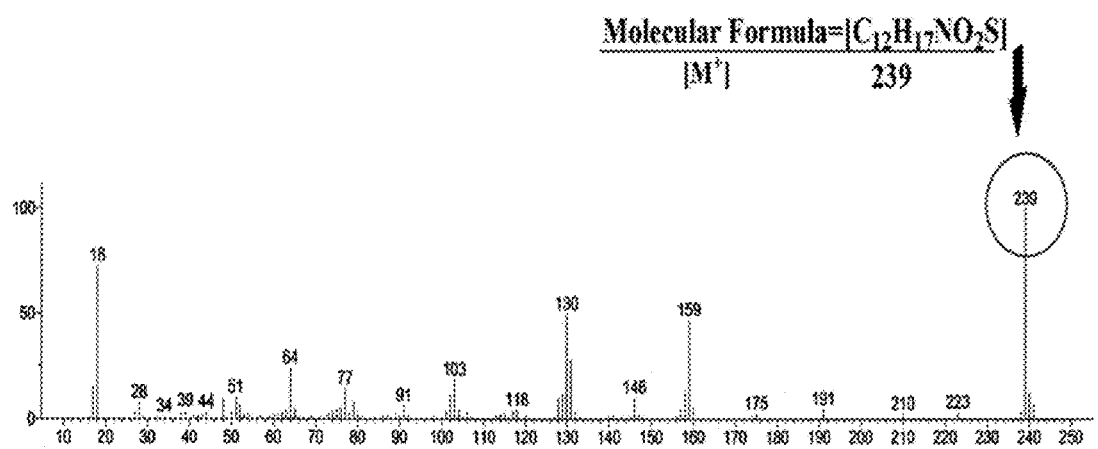
FIG. 12 depicts the mass spectrum of compound (I).

The mass spectra (MS) for compound (I), see FIG. 12, showed the molecular ion peak at m/z 239 (99.9) and the fragments, m/z (%): 239 (99.9) [M$^+$], 223 (3.2), 210 (2.5), 159 (47), 130 (49.8), 103 (18.6), 64 (24.2) and 18 (72.7).

Several methods (methods A, B and C) are used for the preparation of the compound (II) carboxylic acid hydrazides. These methods mainly utilize the carboxylic acid ester with hydrazine or hydrazine derivatives in ethanol. Compound (II), "2-Amino-5,6,7,8-tetrahydro-4H-cyclohepta[b]thiophene-3-carbohydrazide", was prepared via prolonged heating of "2-amino thiophene-3-carboxylate" (I) with excess of hydrazine hydrate in absolute ethanol as solvent by the conventional method, by microwave and by ultrasonic sound.

In accordance with method A, the conventional method, a mixture of compound
(I) (0.24 g, 1 mmol) and excess of hydrazine hydrate (5 mmol) in absolute ethanol (20 ml, 99.9%) was refluxed for 18 hours. The cold reaction mixture was treated with crushed ice (50 ml), the solid product was filtered off, dried and recrystallized by hexane.

In accordance with method B, microwave irradiated method, a mixture of compound (I) (0.24 g, 1 mmol) and hydrazine hydrate (1 ml) and 2 drops of absolute ethanol was exposed to microwave and irradiated at 390 W for 30 minutes. The cold reaction mixture was treated with crushed ice (20 ml), the solid product was filtered off, dried and recrystallized by hexane.

In accordance with method C, the ultrasound irradiated method, compound (I) (0.24 g, 1 mmol) and excess of hydrazine hydrate (5 mmol) in absolute ethanol (10 ml) was irradiated by ultrasound (US) for 4 hours. The cold reaction mixture was treated with crushed ice, the solid product was filtered off, dried and recrystallized by hexane.

Figure 13:
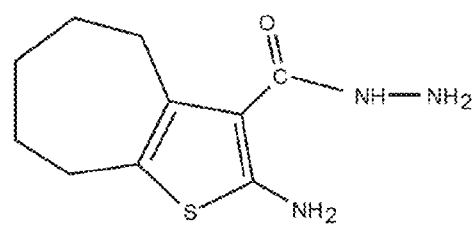
FIG. 13 shows the chemical structure of compound (II).

The structure of compound (II), see FIG. 13, was assigned on the basis of IR, $^1$H-NMR and MS spectral data.

Figure 14:
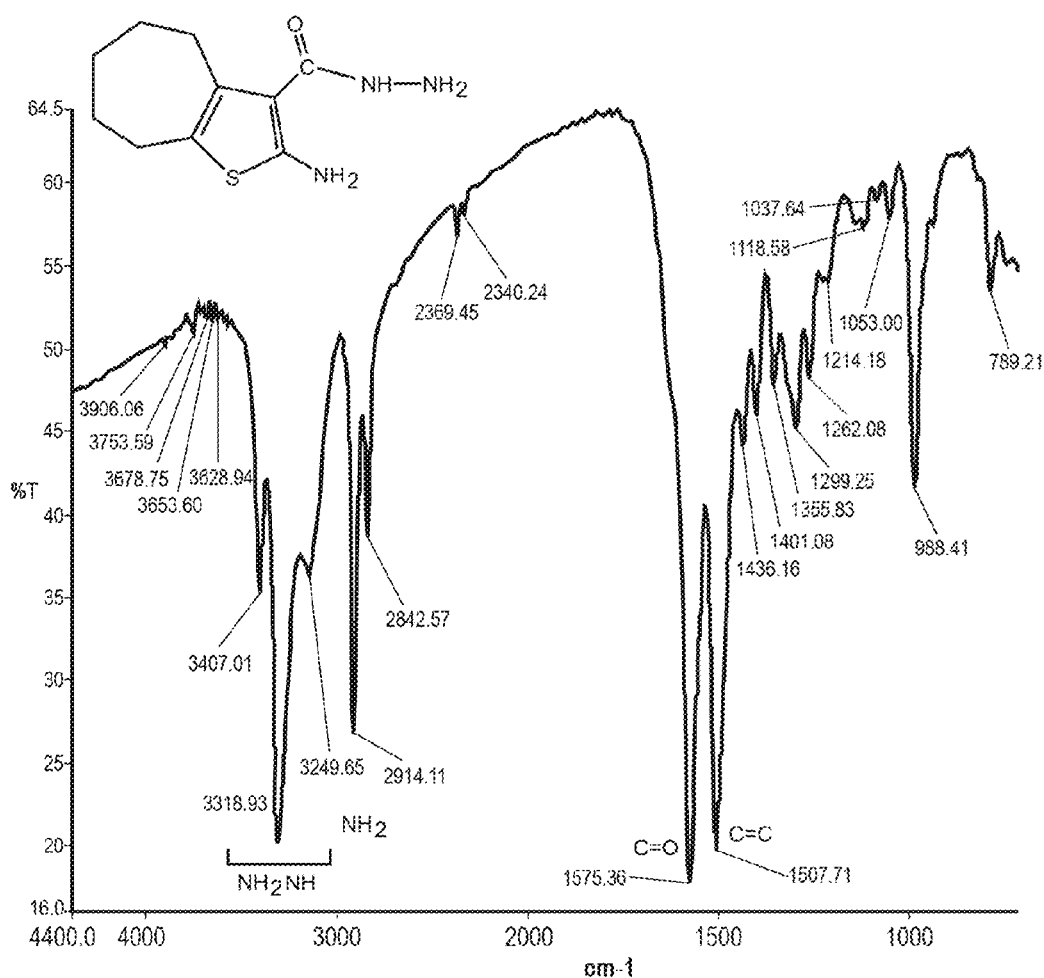
FIG. 14 depicts the infrared spectra of compound (II).

In one test, the infrared spectra (IR) of compound (II) showed absorption peaks at 3407.01, 3313.93, 3419.65 cm$^{-1}$ (2×NH$_2$/NH), 1575.36 cm$^{-1}$ (C=O), and 1507.71 cm$^{-1}$ (C=C). In a more accurate test, the infrared spectra (IR) of compound (II), see FIG. 14, showed absorption peaks at 3441.68, 3340.91, 3222.50 cm-1 (NH$_2$/NH), 1675.95 cm$^{-1}$ (C=O), 1574.21, 1544.06 cm$^{-1}$ (C=C).

Figure 15:
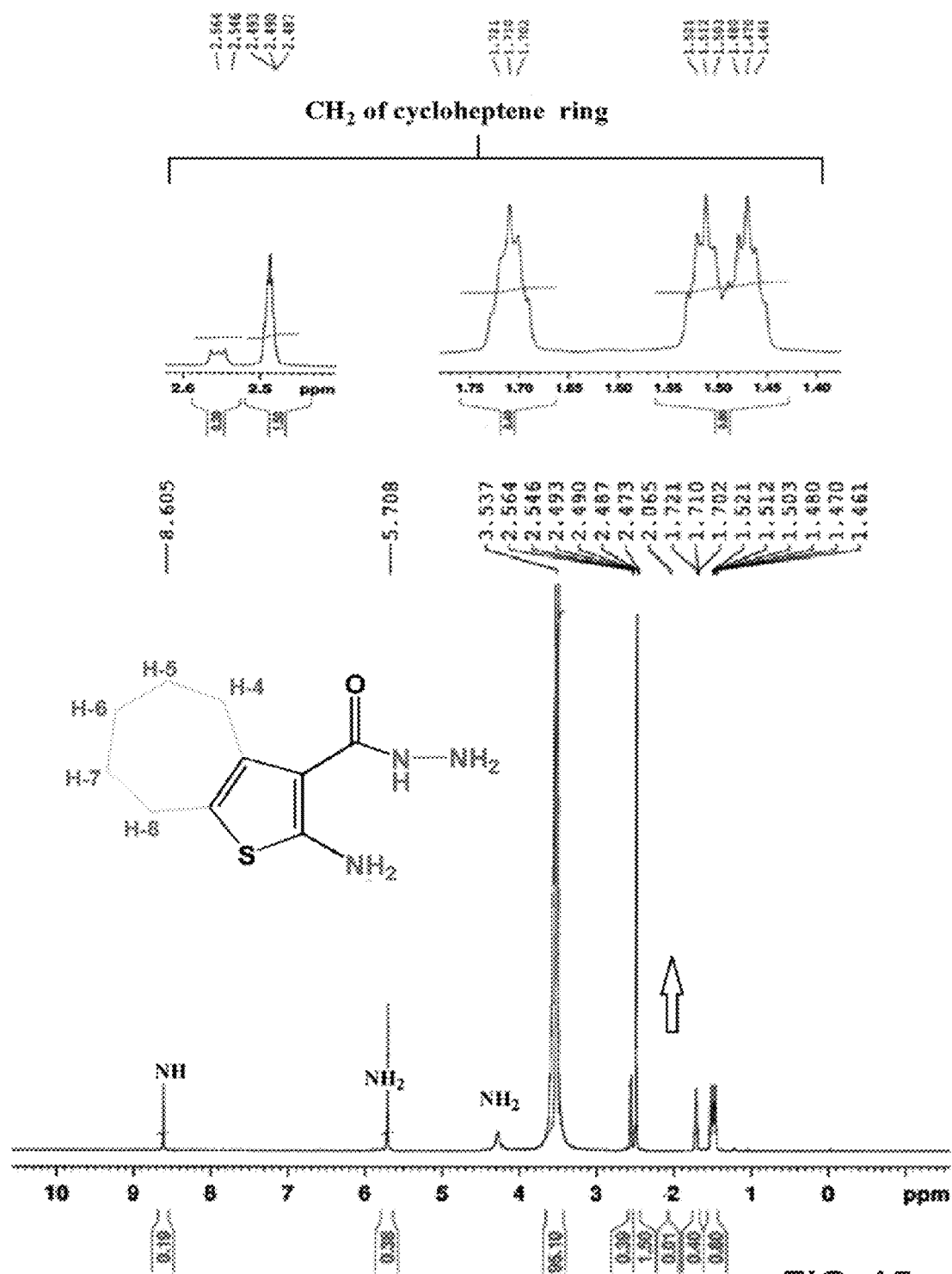
FIG. 15 depicts the nuclear magnetic resonance spectrum of the protons compound (II).

The nuclear magnetic resonance spectra ($^1$H-NMR) of compound (II), see FIG. 15, showed a multiplet at δ1.45-1.53 ppm (4H, H-5,7), a multiplet at δ1.71 ppm (2H, H-6), a triplet at δ2.490 ppm (2H, $^3$J=5.4 Hz, H-8), a triplet at δ2.564 ppm (2H, $^3$J=5.4 Hz, H-4) corresponding to the methylene groups protons in the cycloheptene moiety, while the NH$_2$ and NH protons appeared as a singles at 4.29 ppm (2H), 5.708 ppm (2H), 8.608 ppm (1H) respectively.

Figure 16:
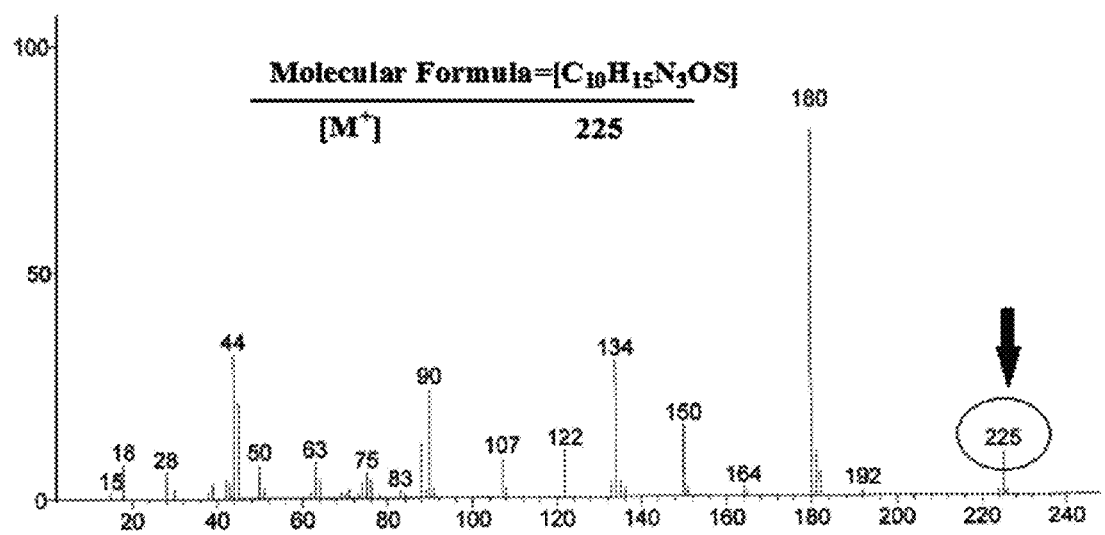
FIG. 16 depicts the mass spectrum of compound (II).

The mass spectra (MS) for compound (II), see FIG. 16, showed the molecular ion peak at m/z 225 (9.7) and the fragments, m/z (%): 225 (9.7) [M$^+$], 192 (1.4), 180 (99.9), 150 (15.7), 134 (30.2), 107 (8.8), 90 (24.1) and 44 (31.8).

Two methods (methods A and B) are used for the preparation of compound (III). The most widely utilized method for the preparation of the compound III derivative, "3-Amino-2-thioxo-2,3,6,7,8,9-hexahydro-1H-cyclohepta[4,5]thieno[2,3-d]pyrimidin-4(5H)-one" depends on the condensation of carboxylic acid hydrazide with carbon disulphide. Compound (III) was prepared by heating the "2-amino3-carbohydrazide" (II) with carbon disulphide in dry pyridine on water-bath or ultrasonic sound.

In accordance with method A, the traditional heating method, compound (II) (0.23 g, 1 mmol) in pyridine (20 ml) and carbon disulfide (0.39 g, 5 mmol) was added and mixture was heated on water-bath for 21 hours. After cooling, ethanol was added and the green separated solid was collected by filtration and washed with methanol.

In accordance with method B, the ultrasound Irradiated method, compound (II) (0.23 g, 1 mmol) in pyridine (10 ml) and carbon disulfide (0.39 g, 5 mmol) was irradiated by ultrasound (US) for 8 hours. After cooling, ethanol was added and the green separated solid was collected by filtration and washed with methanol.

Figure 17:
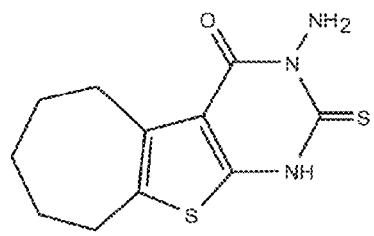
FIG. 17 shows the chemical structure of compound (III).

The chemical structure of compound (III) is shown in FIG. 17.

Figure 18:
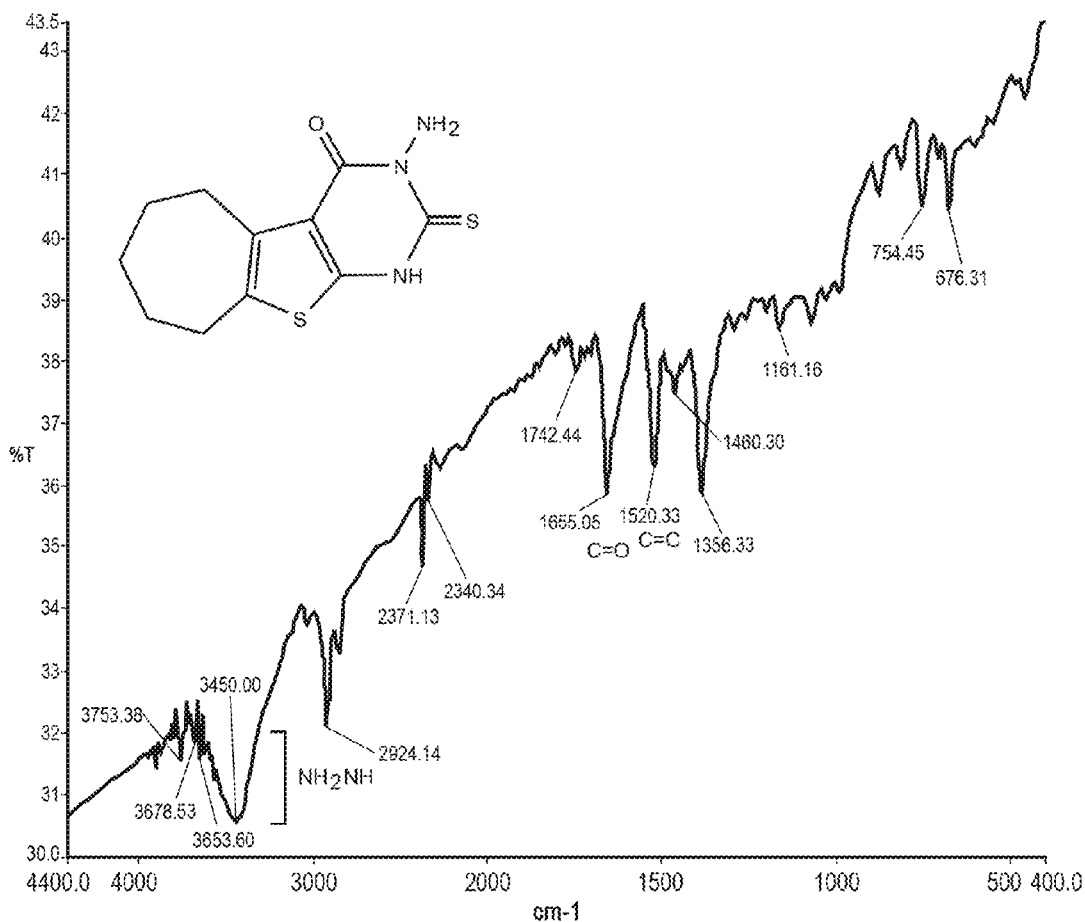
FIG. 18 depicts the infrared spectra of compound (III).

The infrared spectra (IR) of compound (III), see FIG. 18, showed absorption peaks at 3450.00 cm$^{-1}$ (NH$_2$/NH), 1655.05 cm$^{-1}$ (C=O), 1520.33 cm$^{-1}$ (C=C).

Figure 19:
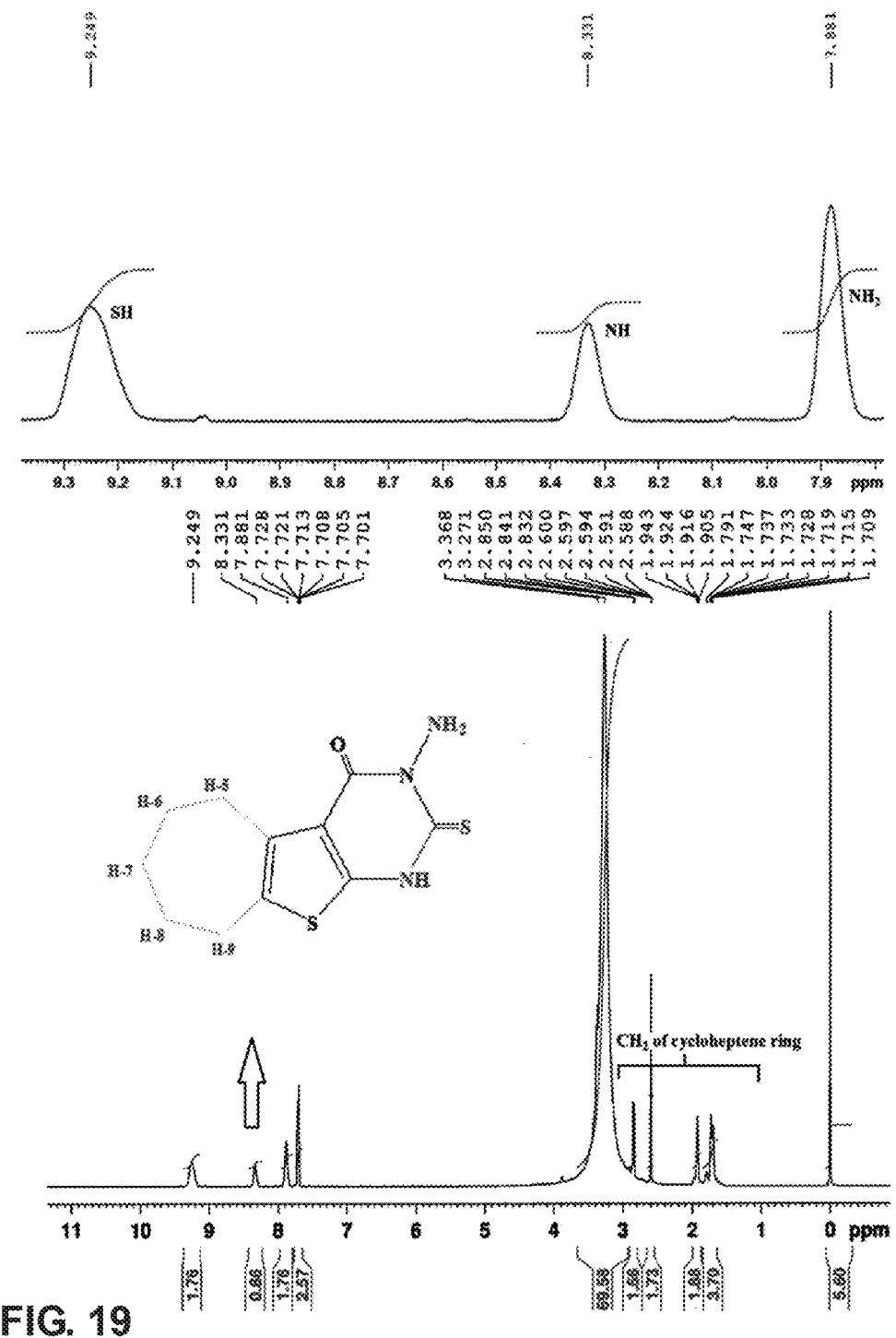
FIG. 19 depicts the nuclear magnetic resonance spectrum of the protons compound (III).

The nuclear magnetic resonance spectra ($^1$H-NMR) of compound (III), see FIG. 19, are characterized by the presence of cycloheptene protons as a multiplet at δ0.696-1.791 ppm (4H, H-6,8), a multiplet at 1.92 ppm (2H, H-7), a triplet at δ2.59 ppm (2H, $^3$J=5.4 Hz, H-9), a triplet at δ 2.84 ppm (2H, $^3$J=5.4 Hz, H-5). In addition, the NH$_2$ and NH protons appeared at δ7.88 ppm (s, 2H), 8.33 (s, 1H), ppm, respectively, while the SH proton appeared as a singlet at 9.249 ppm.

Figure 20:
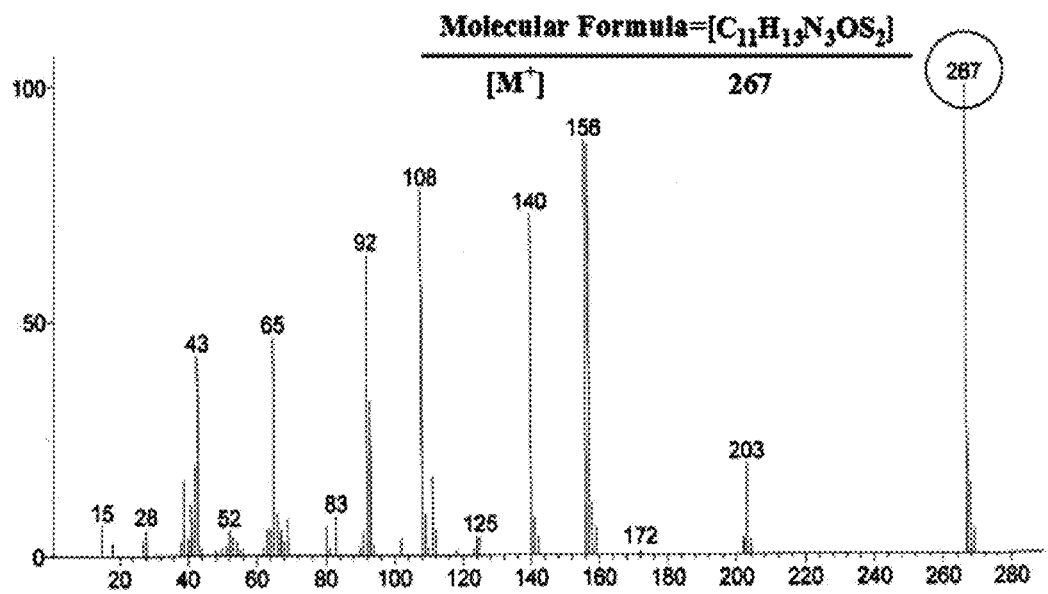
FIG. 20 depicts the mass spectrum of compound (III).

The mass spectra (MS) for compound (III), see FIG. 20, showed the molecular ion peak at m/z 267 (99.9), and the fragments, m/z (%): 267 (99.9) [M$^{+1, 203}$] (19.4), 172 (1.2), 156 (88.3), 140 (72.6), 108 (77.9), 92 (94) and 65 (46.5).

Several methods were reported for the synthesis of "thieno[2,3-d][1,3,4]thiadiazolo[3,2-a]pyrimidine", utilizing "thieno[2,3-d]pyrimidine" as a starting material. The compound of the invention, "2-((4-Nitrophenyl)amino)-7,8,9,10-tetrahydrocyclohepta[4,5]thieno[2,3-d][1,3,4]thiadiazolo[3,2-a]pyrimidin-11(6H)-one", was prepared by the reaction of compound (III) with "4-nitrophenyl isothiocyanate" in dry "N,N-dimethyl formamide" (DMF) as solvent by conventional heating method, by microwave and by ultrasonic sound.

In accordance with method A, the traditional heating method, 4-nitro phenyl isothiocyanate (2 mmol) was added to a solution of compound (III) (0.27 g, 1 mmol) in dry DMF (20 ml) and the solution was heated under reflex for 10 hours. On cooling, the mixture was poured onto cold water (60 ml) and the separated precipitate was filtered, washed with water, dried and recrystallized by hexane.

In accordance with method B, the microwave irradiated method, a mixture of compound (III) (0.27 g, 1 mmol) and 4-nitrophenylisothio cyanate (2 mmol) in DMF was placed in a 50 ml beaker covered with a watch glass and then irradiated with microwaves (520 W) for 2 minutes. On cooling, the mixture was poured onto cold water (10 ml) and the separated precipitate was filtered, washed with water, dried and recrystallized by hexane.

In accordance with method C, the ultrasound irradiated method, compound (III) (0.27 g, 1 mmol) in DMF (10 ml) and 4-nitrophenylisothiocyanate (2 mmol) was irradiated by ultrasound (US) for 4 hours. After cooling, water (30 ml) was added and the separated solid was collected by filtration and washed with water, dried and recrystallized by hexane.

Figure 21:
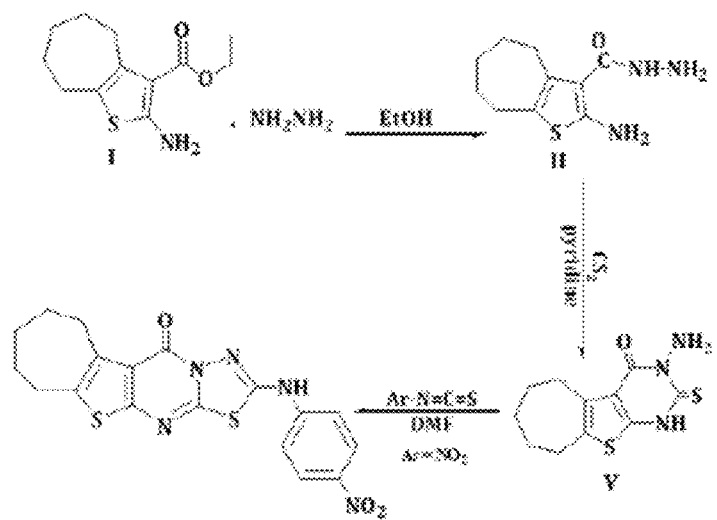
FIG. 21 shows the series of chemical reactions that produce the chemical compound of the invention.
Figure 22:
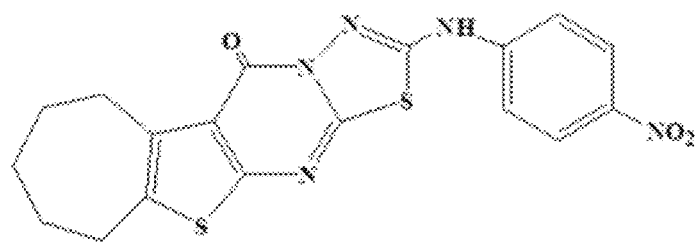
FIG. 22 shows the chemical structure of the compound of the invention.

FIG. 21 shows the series of chemical reactions with compounds I, II and III that produce the compound of the invention.

The chemical structure of the compound of the invention is shown in FIG. 22.

The structure of the compound of the invention was assigned on the basis of IR, $^1$H-NMR and mass spectral data.

Figure 23:
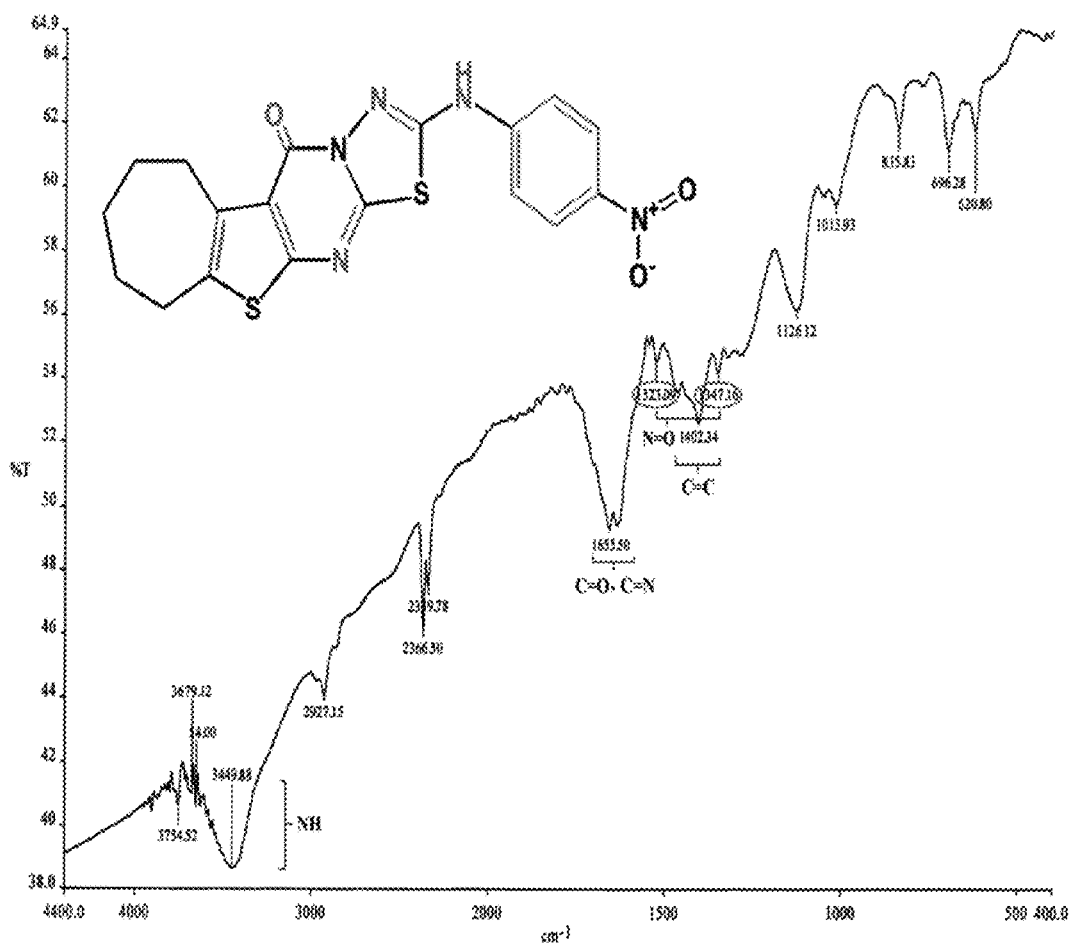
FIG. 23 depicts the infrared spectra of the chemical compound of the invention.

The infrared spectra (IR) of the compound of the invention, see FIG. 23, showed absorption peaks at 3449.88 cm$^{-1}$ (NH), 1655.50 cm$^{-1}$ (C=O, C=N), 14024.34 cm$^{-1}$ (C=C), 1523.09, and 1347.16 cm$^{-1}$ (N=O).

Figure 24:
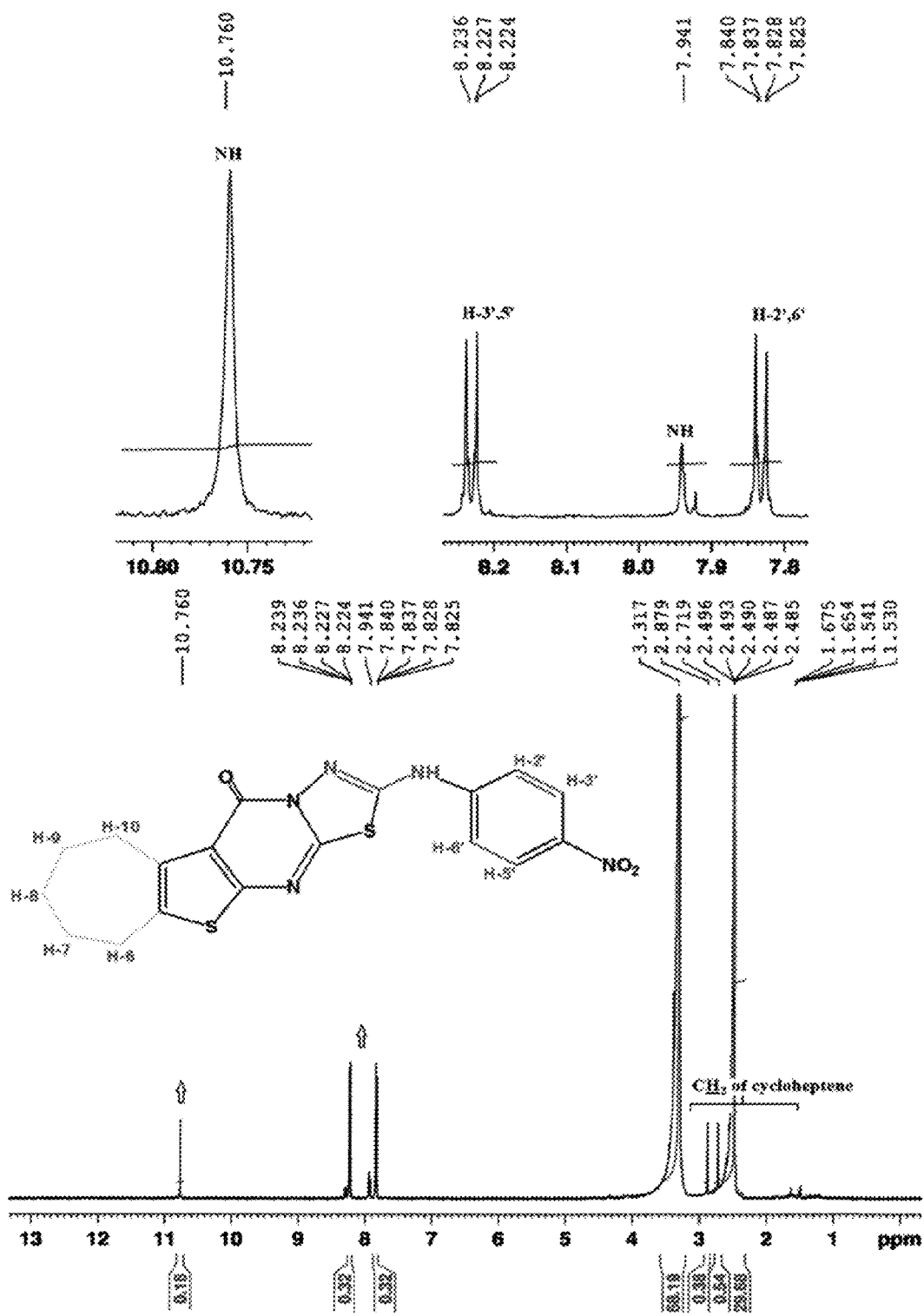
FIG. 24 depicts the nuclear magnetic resonance spectrum of the protons of the compound of the invention.

The nuclear magnetic resonance spectra ($^1$H-NMR) of the compound of the invention, see FIG. 24, are characterized by the presence of cycloheptene protons as a multiplet at δ1.53-1.68 ppm (6H, H-7,8,9), a single at δ2.72 ppm (2H, H-6), a single at δ2.88 ppm (2H, H-10). In addition to two doublet signals, each integrated two protons at δ7.83 ppm ($^3$J=7.2 Hz, $^4$J=1.8 Hz) and at δ8.23 ppm ($^3$J=7.2 Hz, $^4$J=1.8 Hz) due to the protons of the 4-nitro benzene ring (H-2' and H-6') and (H-3' and H-5') respectively. The NH tautomers appeared as singles at δ7.94 and 10.76 ppm, respectively.

Figure 25:
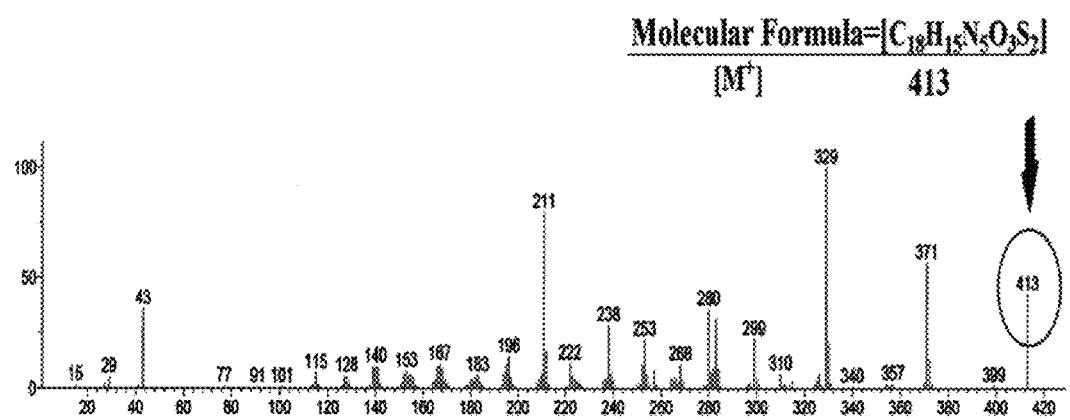
FIG. 25 depicts the mass spectrum of the compound of the invention.

The mass spectra (MS) for the compound of the invention, see FIG. 25, showed the molecular ion peak at m/z 341 (42.5) and the fragments, m/z (%): 341 (42.5) [M$^+$], 399 (1.5), 271 (56.8), 357 (2.2), 329 (99.9), 280 (35.7), 211 (79.9) and 77 (1.4).

Different spectrum techniques have been used to prove the synthesis and making of the above mentioned compounds.

Table 1 shows the physical properties of the above-mentioned compounds.

TABLE 1

| Comp | Mol. Formula | Yield | M.P °C. | Solvent of recrystallization | Color |
|---|---|---|---|---|---|
| I | C$_{12}$H$_{17}$NO$_2$S (239) | 82% | 85 | Petroleum ether 60-80° C. | Orange |
| II | C$_{10}$H$_{15}$N$_3$OS (225) | 53% | 164 | Hexane | White |
| III | C$_{11}$H$_{13}$N$_3$OS$_2$ (267) | 66% | 98 | Methanol | Green |
| IV | C$_{18}$H$_{15}$N$_5$O$_3$S$_2$ (413) | 52% | >300 | Hexane | Yellow |

Figure 26:
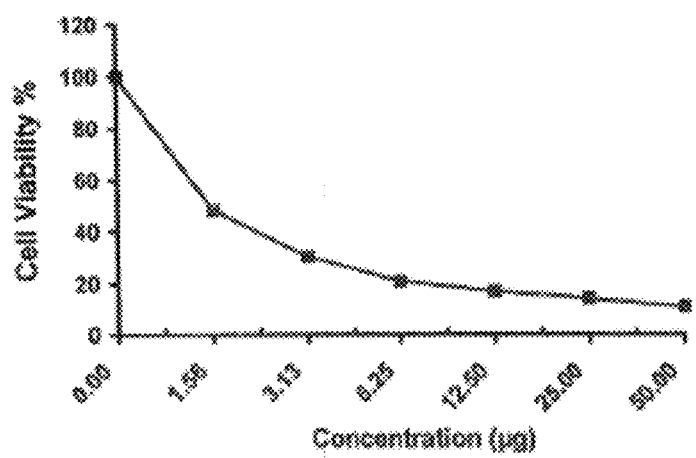
FIG. 26 is a graph of the cytotoxicity of Doxorubicin against HepG2.
Figure 27:
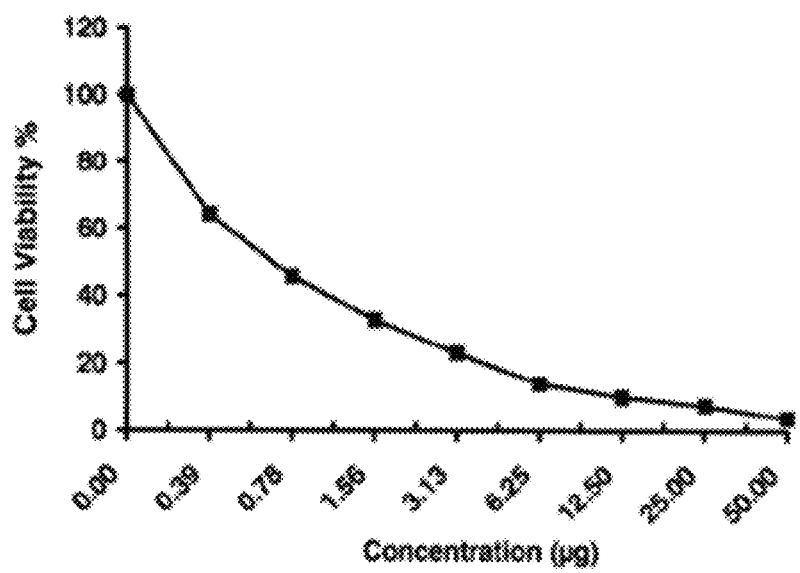
FIG. 27 is a graph of the cytotoxicity of the chemical compound of the invention against HepG2.
Figure 1:
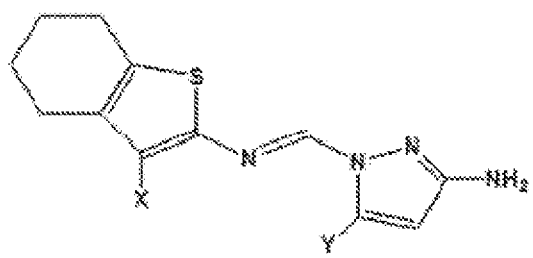
Figure 2:
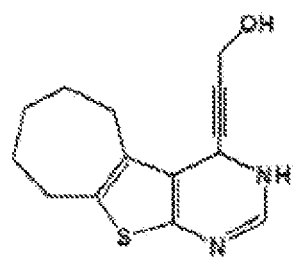
Figure 3:
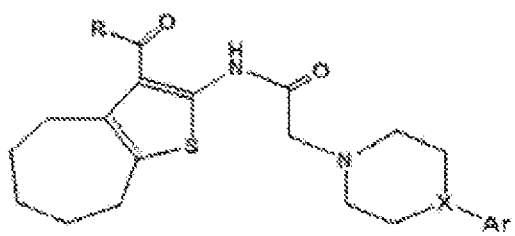
Figure 4:
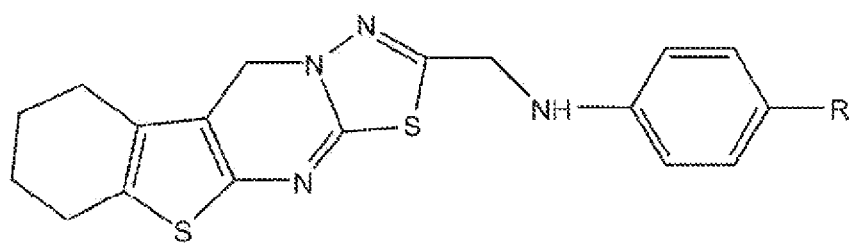
Figure 5:
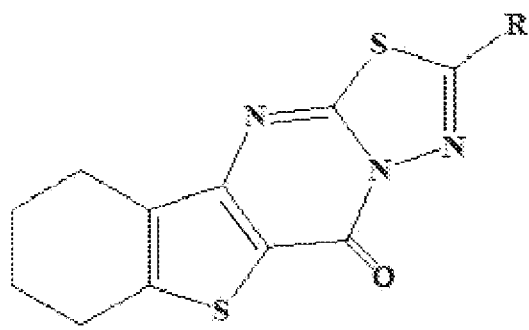
Figure 6:
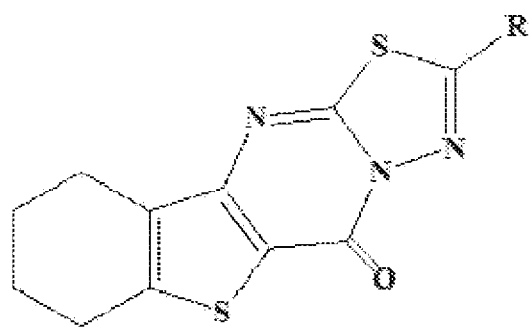
Figure 7:
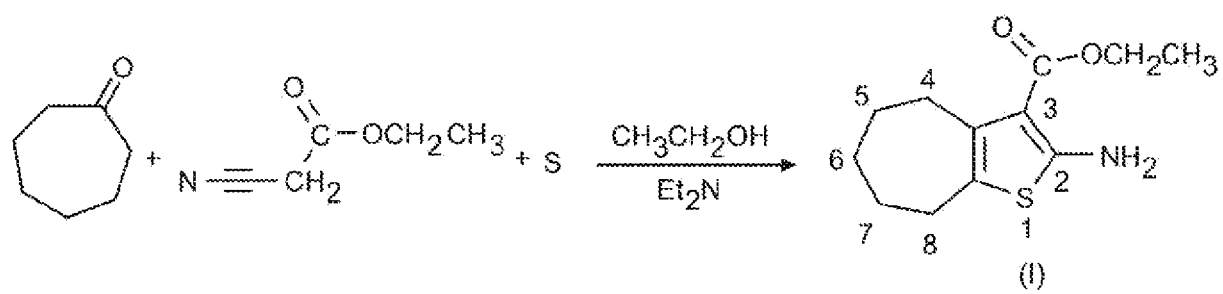
Figure 8:
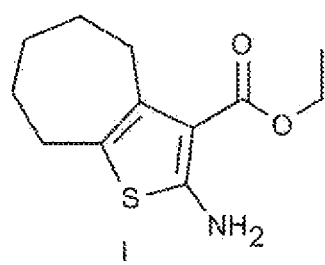
Figure 9:
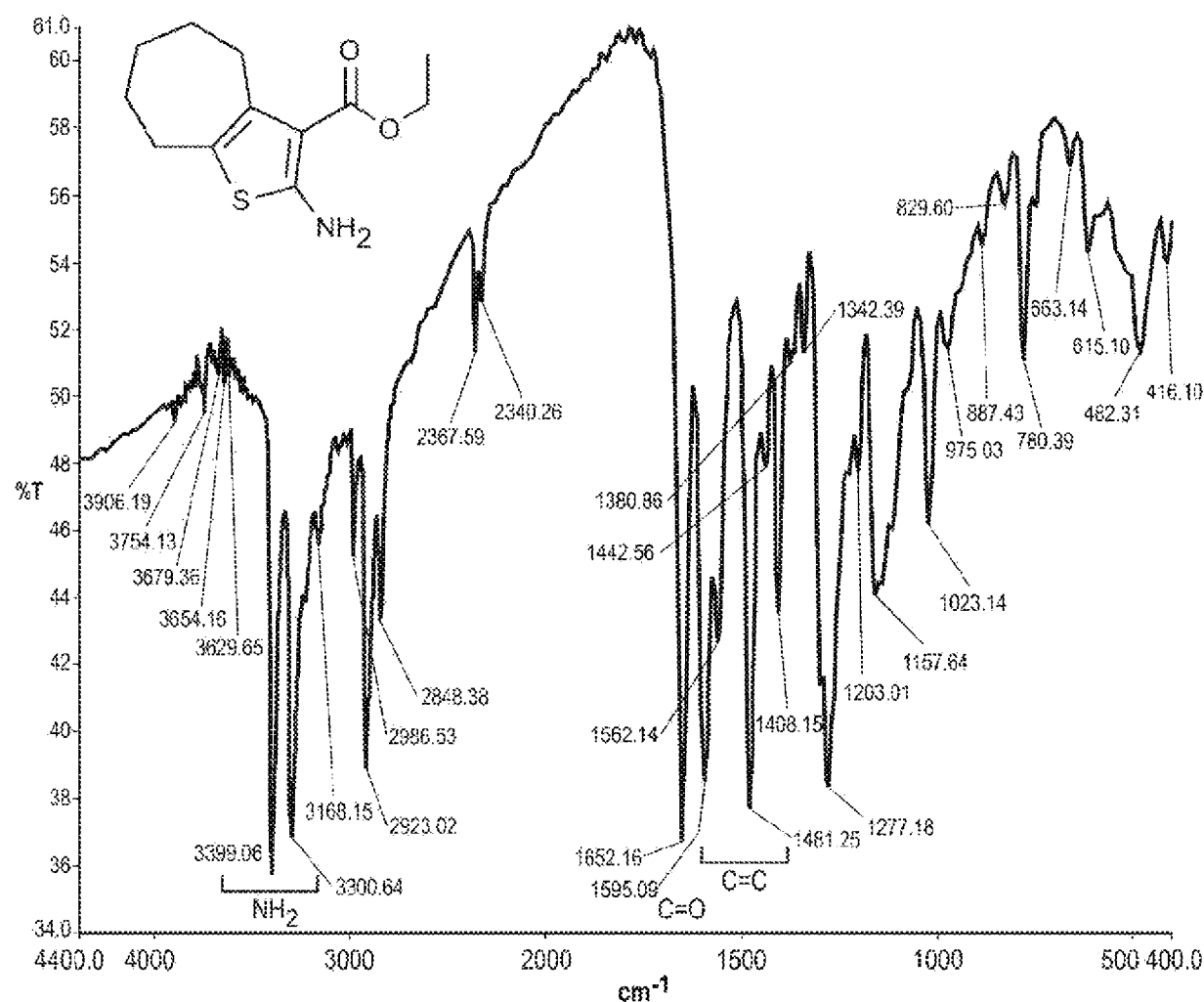
Figure 10:
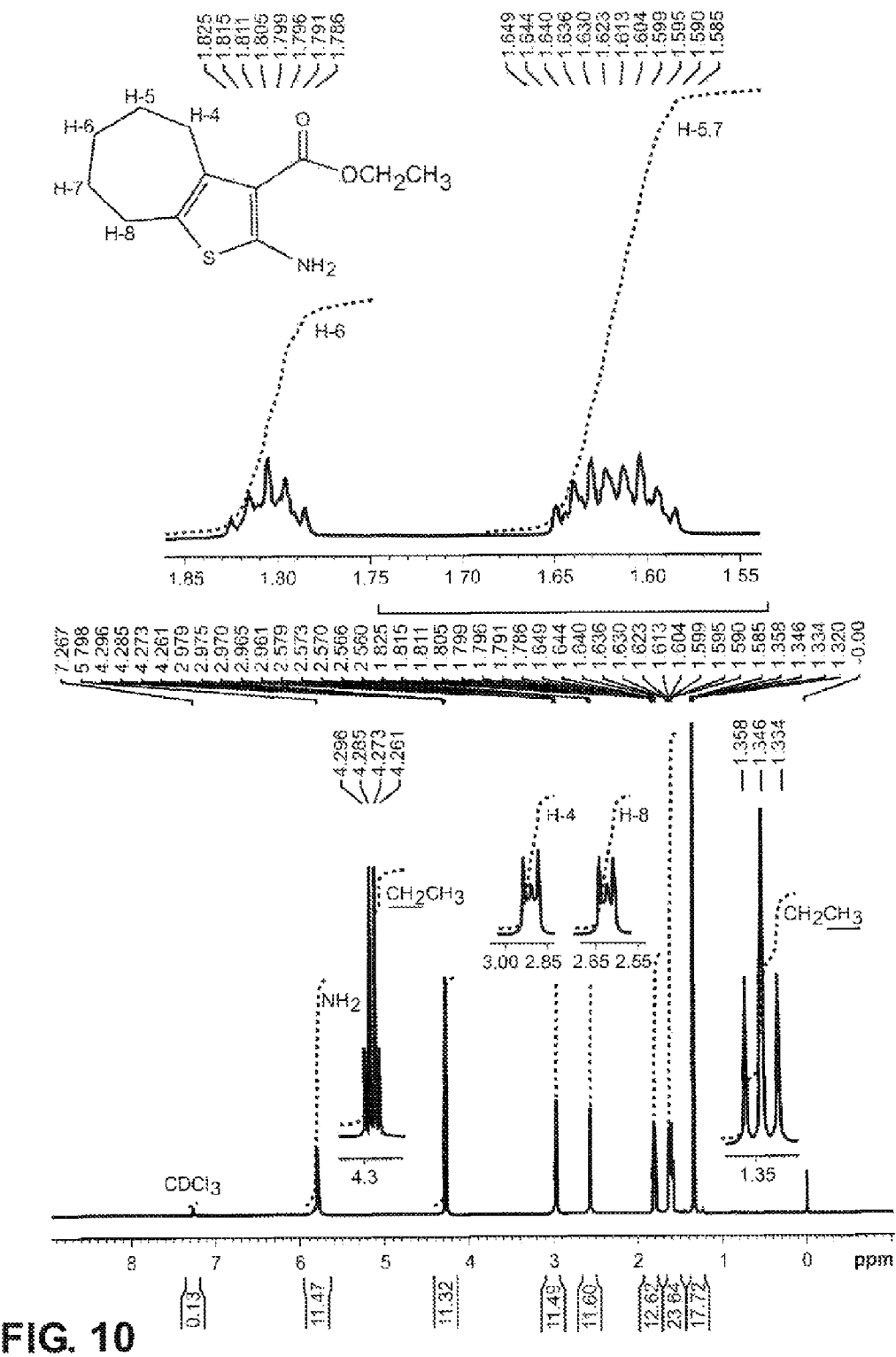
Figure 11:
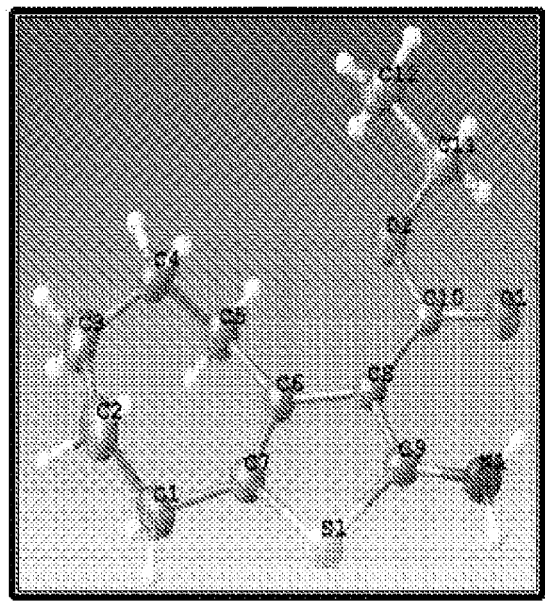
Figure 12:
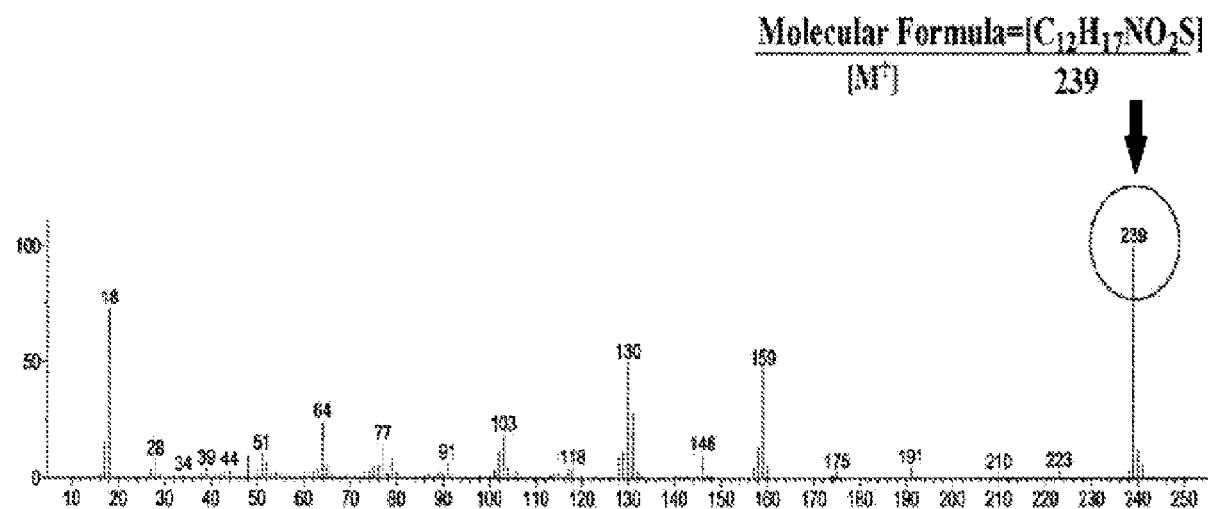
Figure 13:
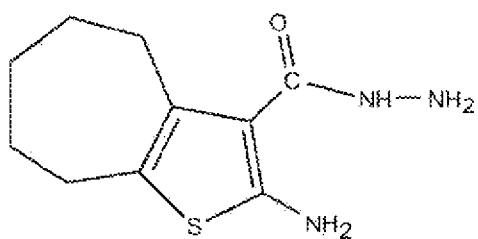
Figure 14:
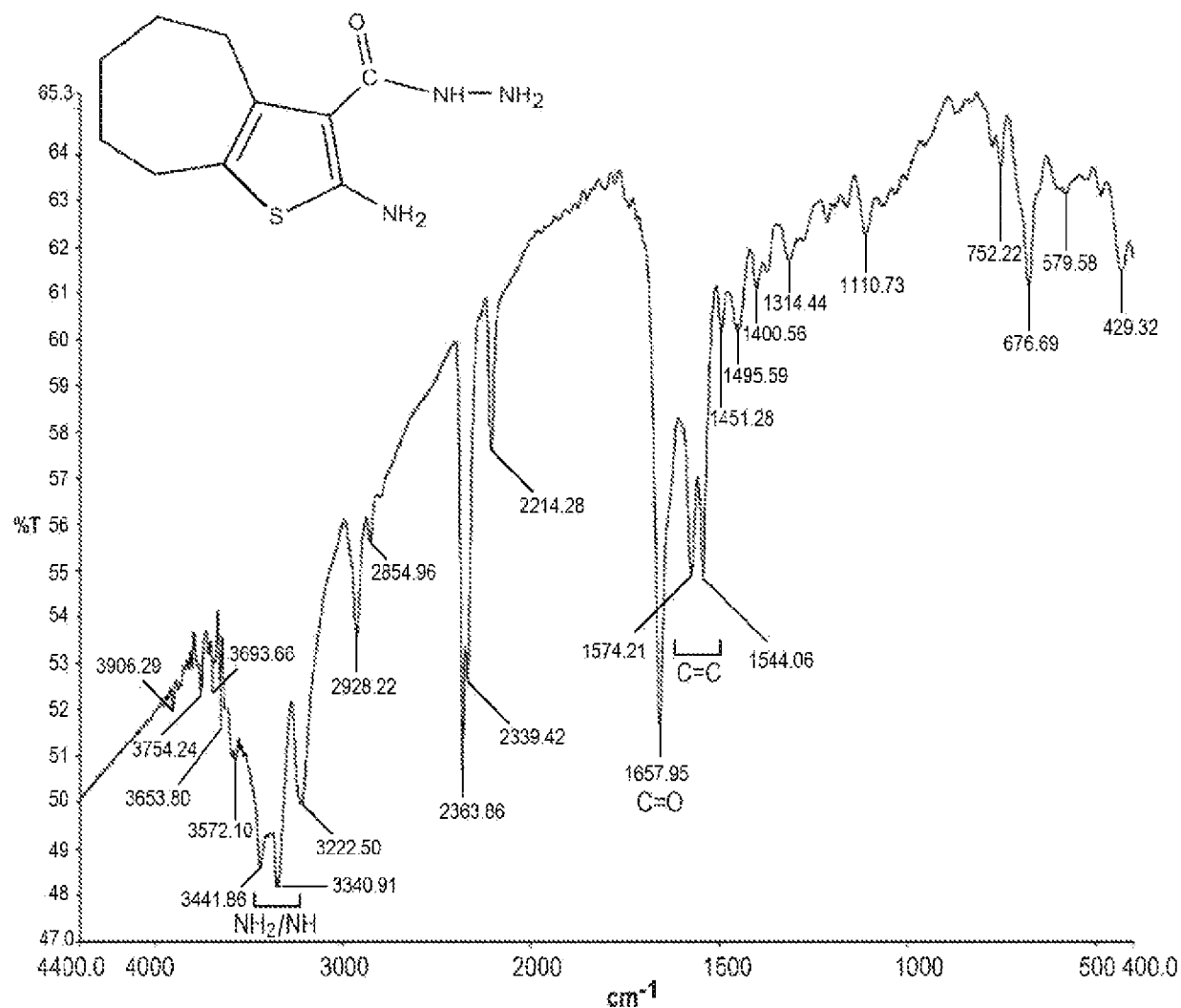
Figure 15:
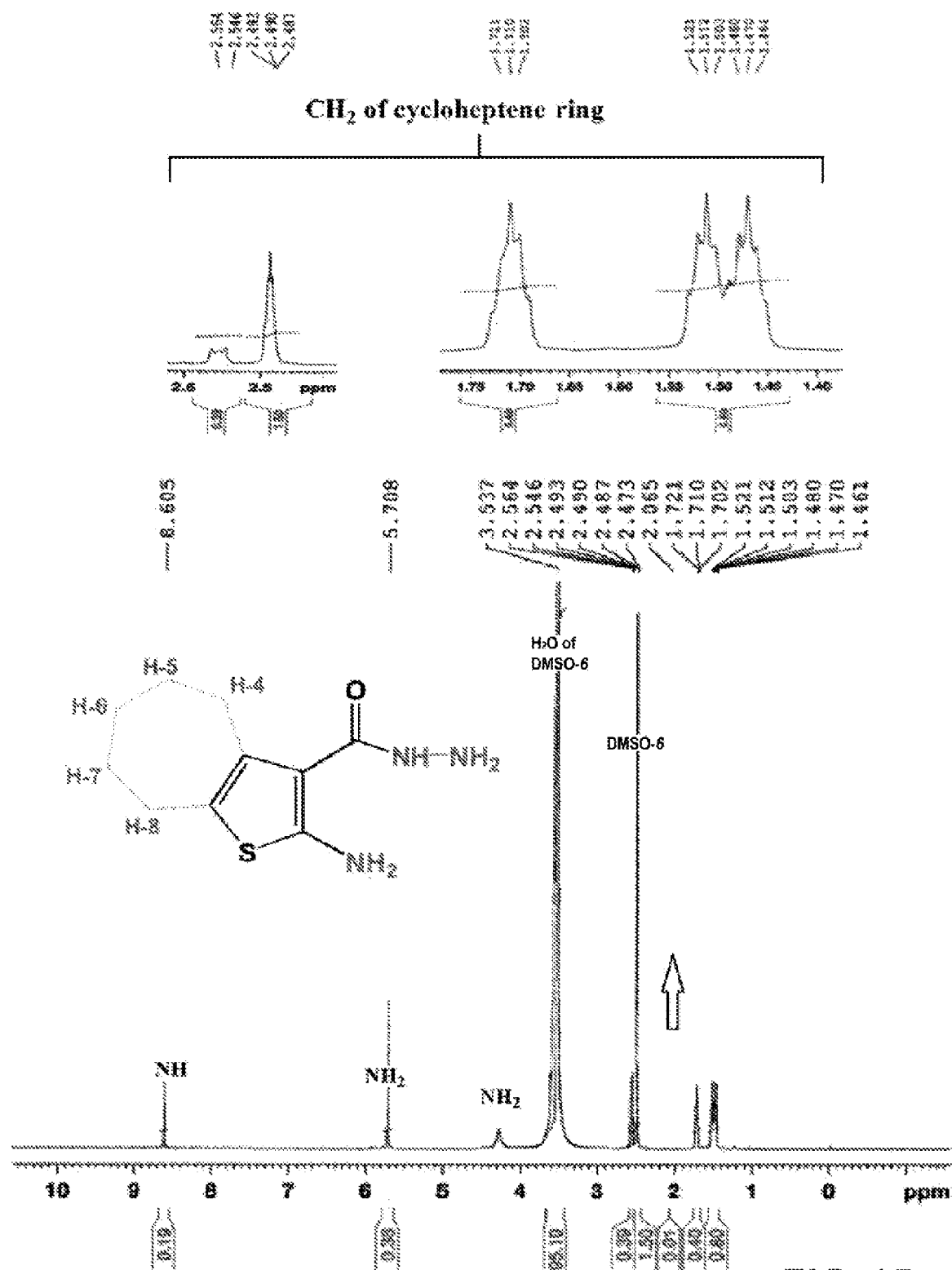
Figure 16:
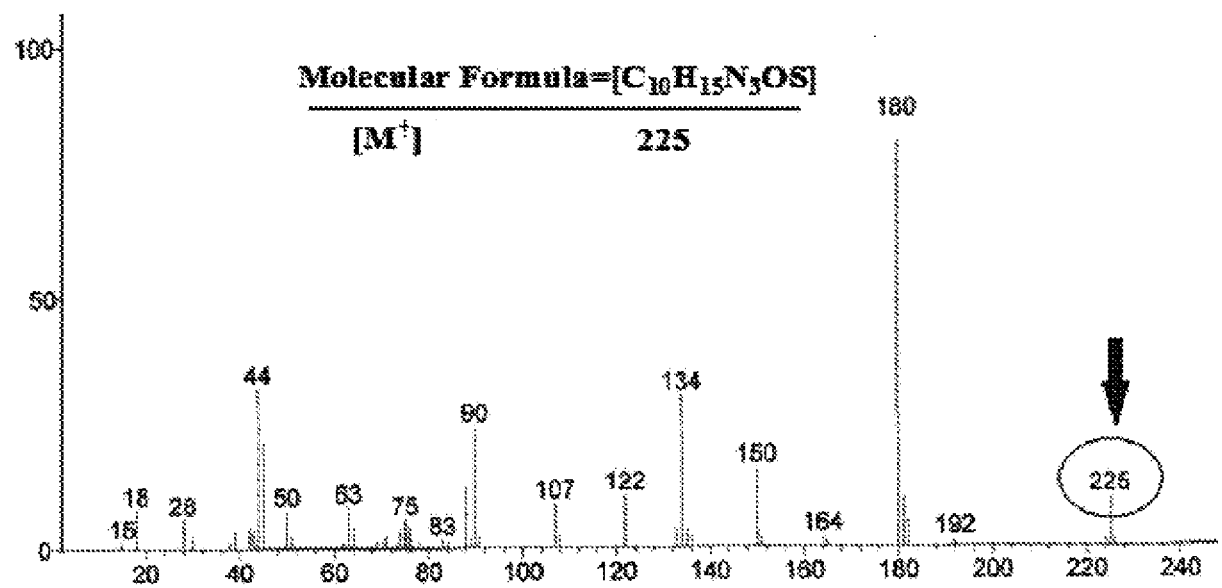
Figure 17:
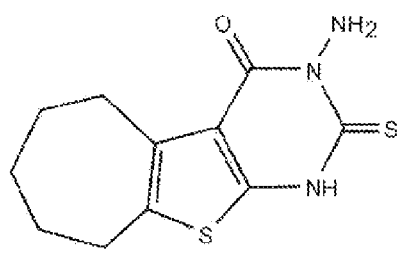
Figure 18:
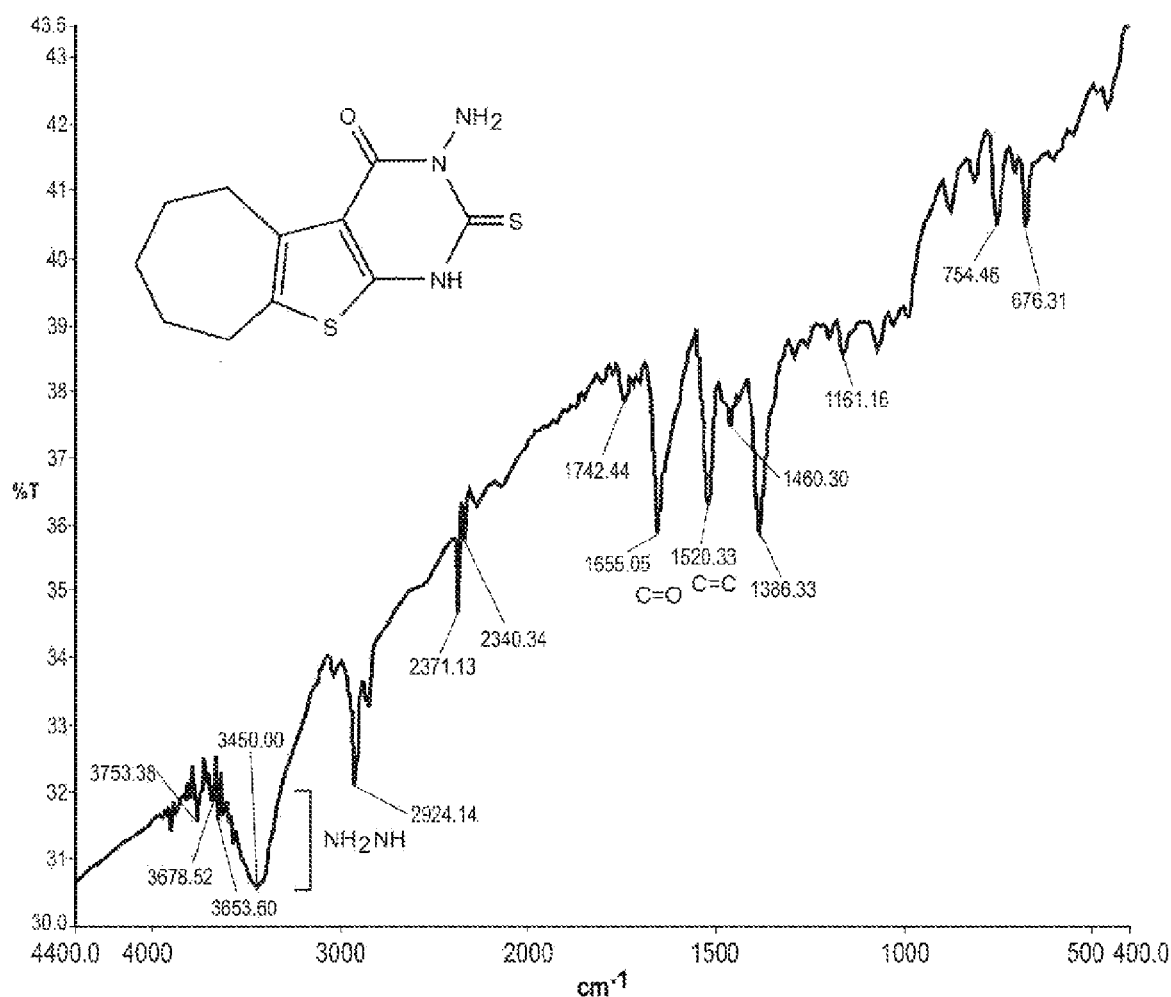
Figure 19:
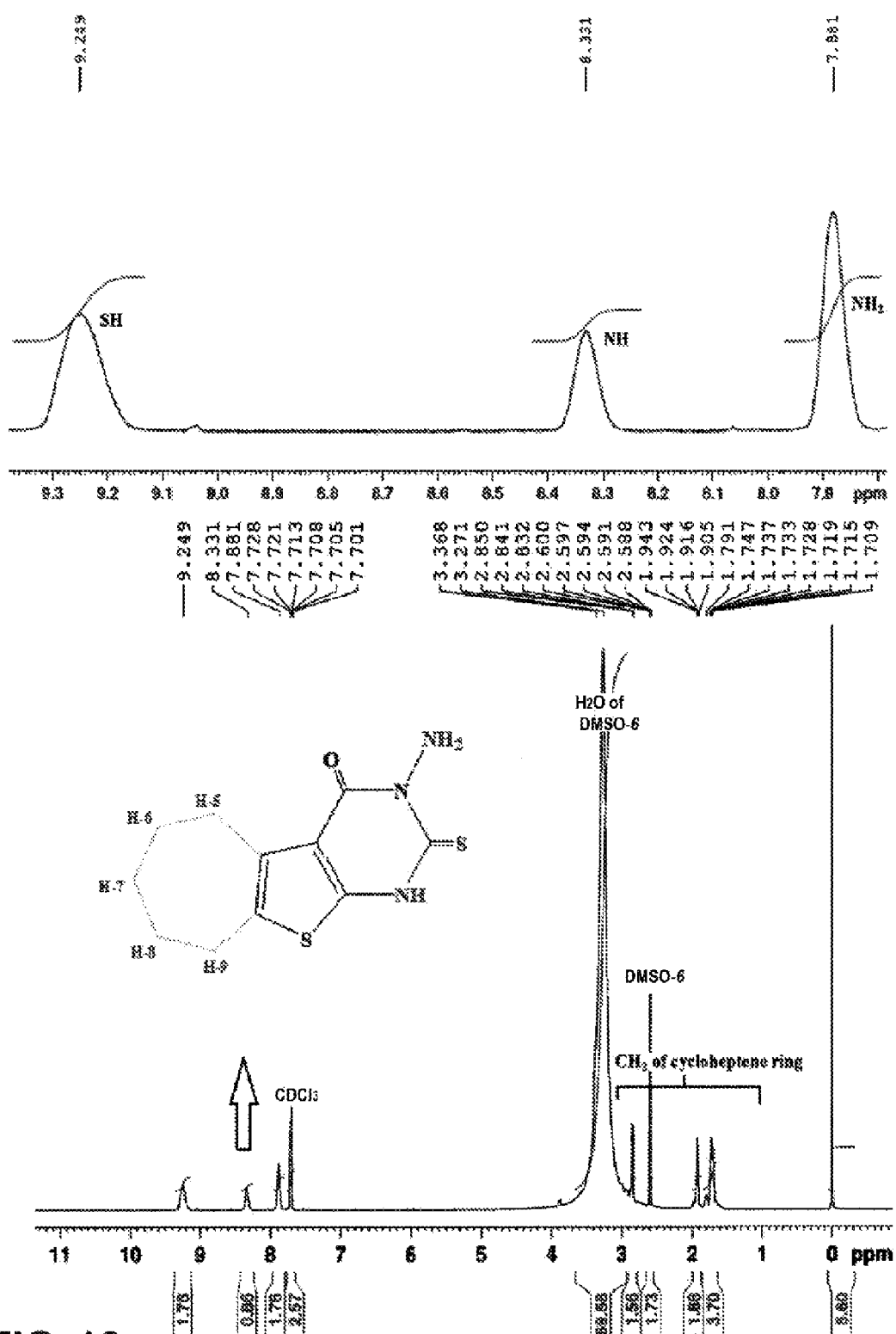
Figure 20:
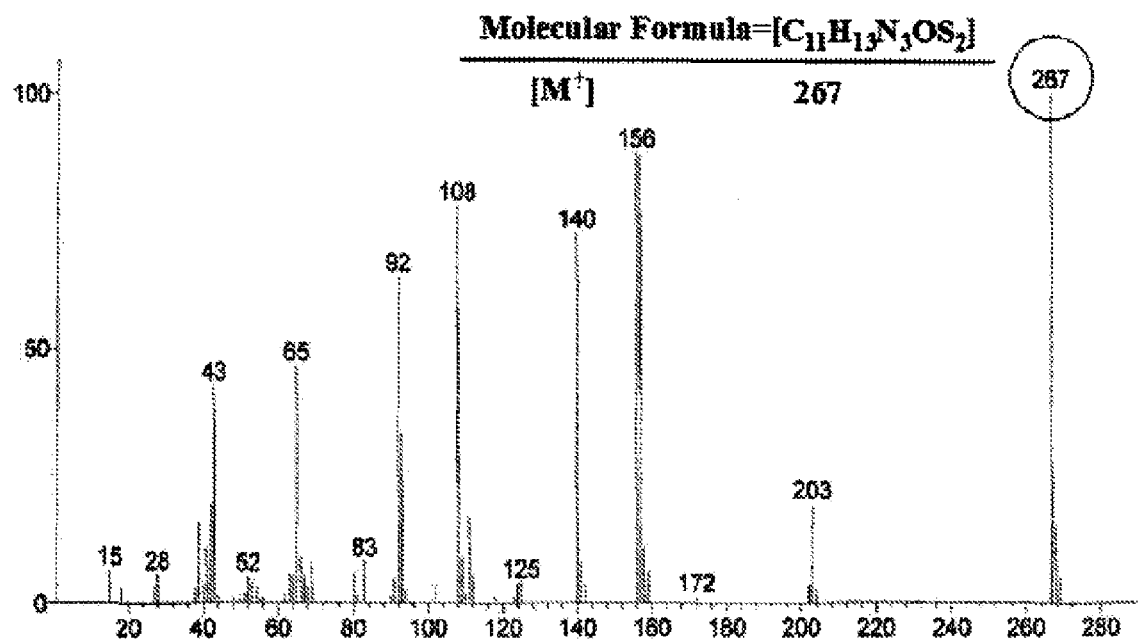
Figure 21:
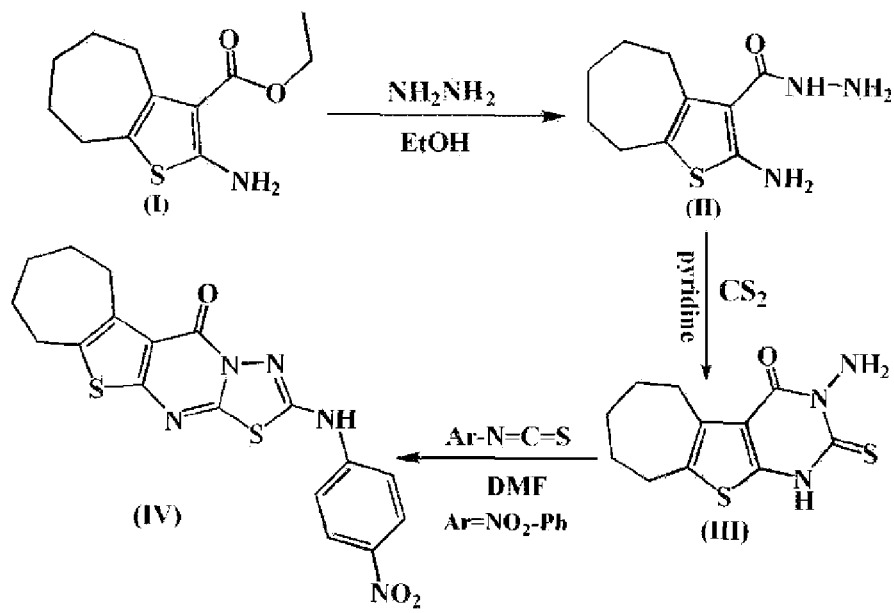
Figure 22:
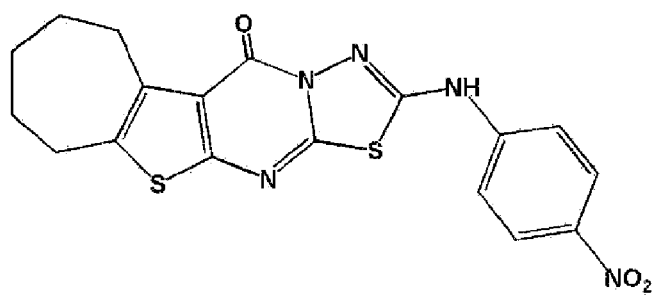
Figure 23:
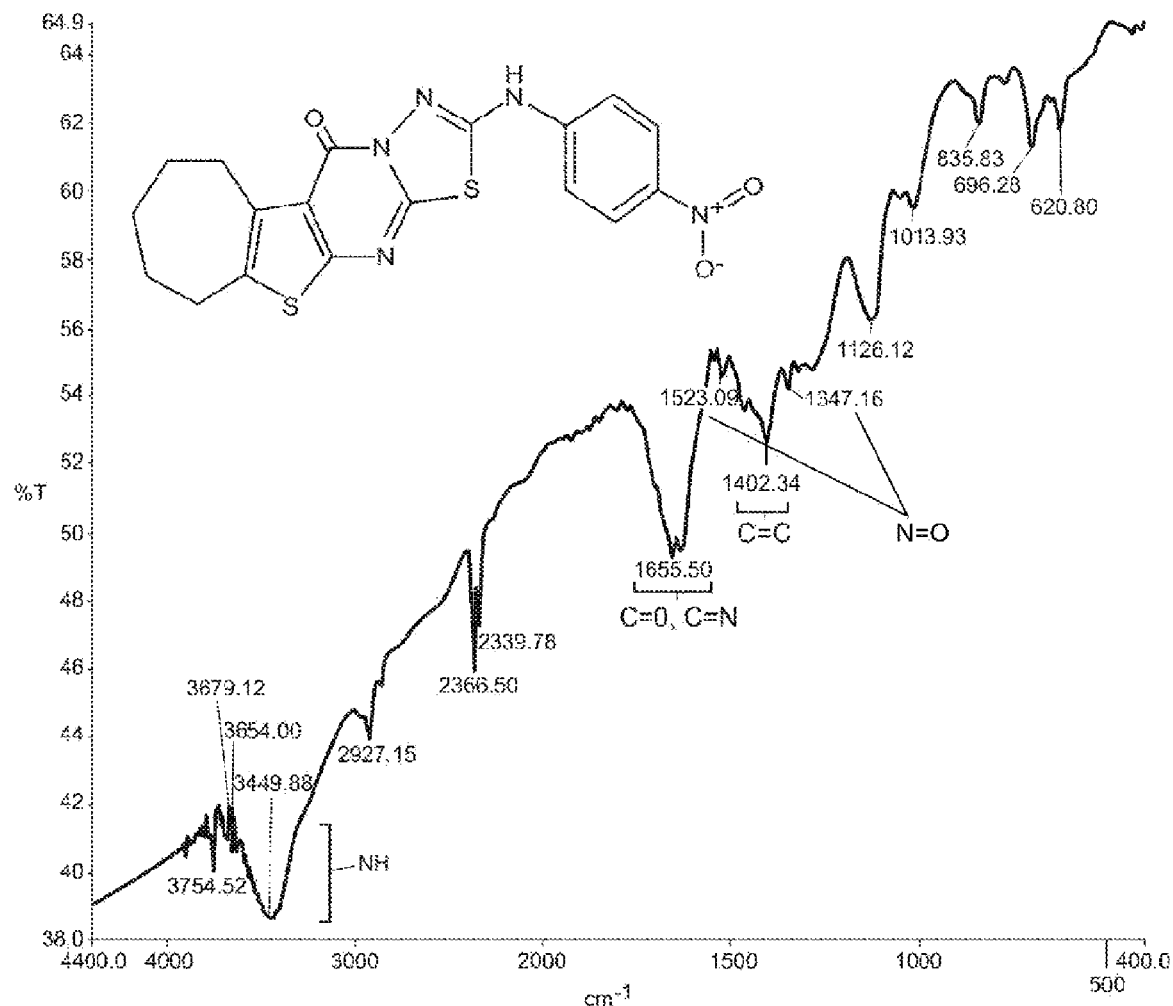
Figure 24:
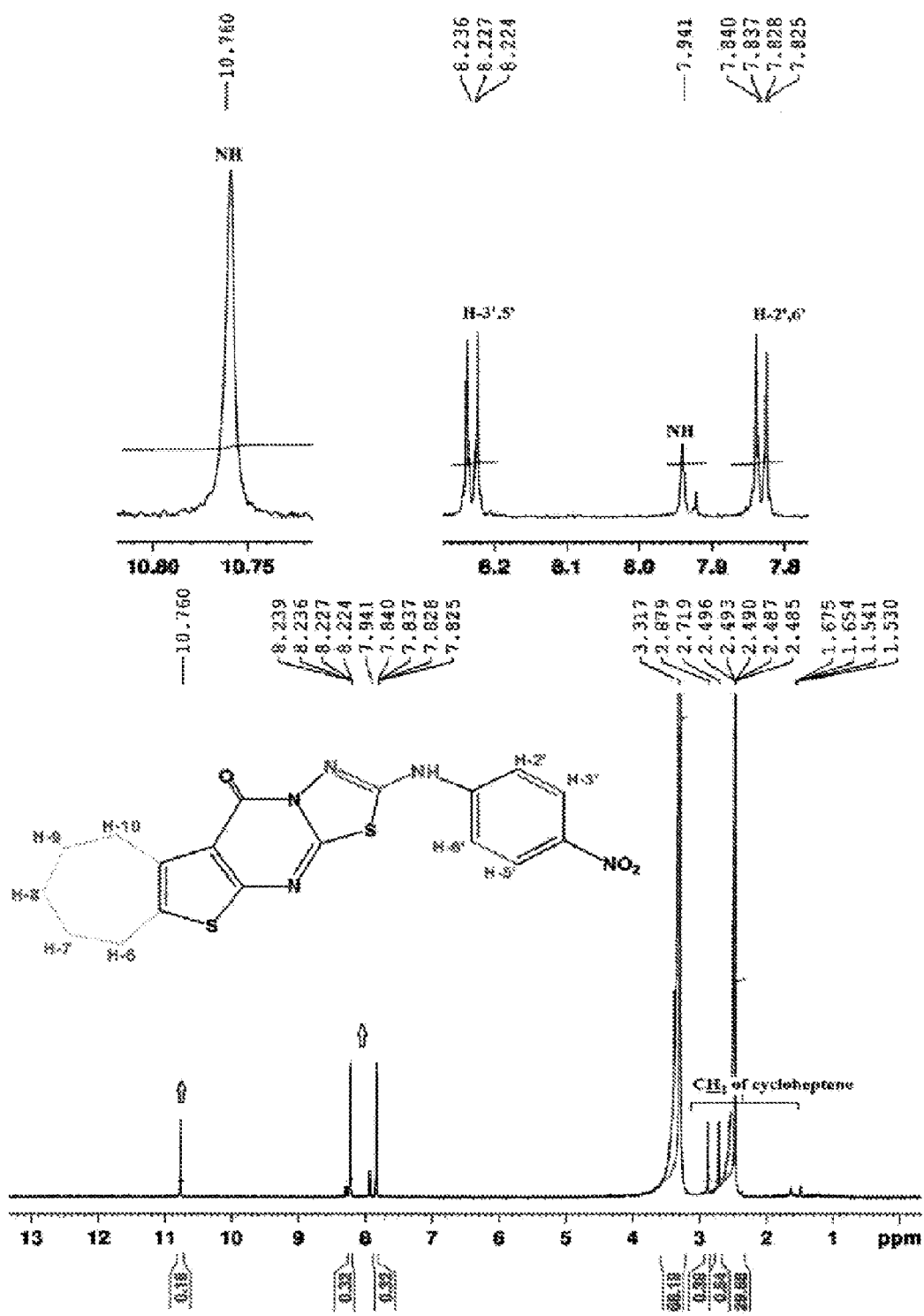
Figure 25:
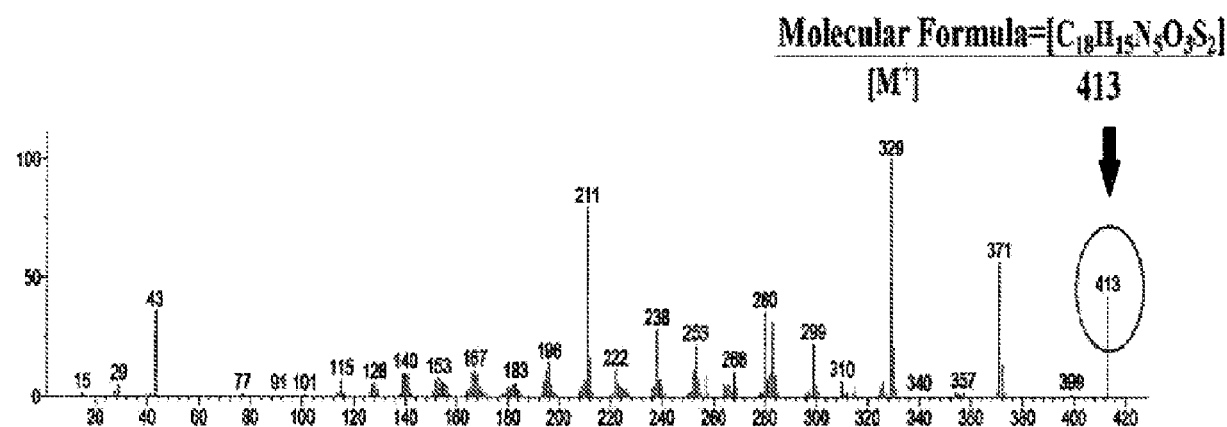
Figure 26:
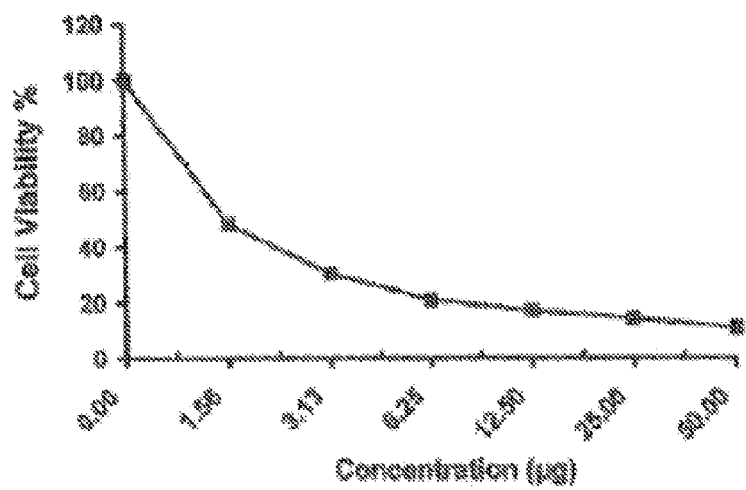
Figure 27:
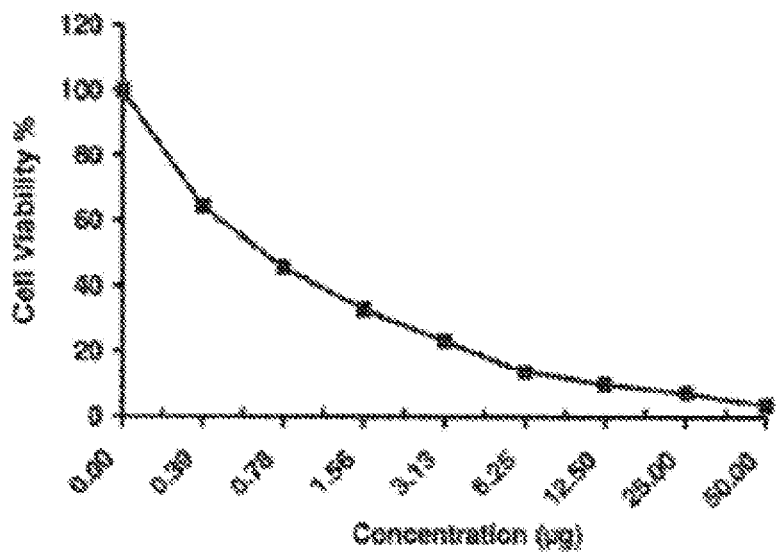

Evaluation of the cytotoxicity of the Doxorubicin standard and the compound of the invention against the HepG2 cell line are shown in FIGS. 26 and 27 and in tables 2 and 3.

HepG2 cells (human cell line of a well differentiated hepatocellular carcinoma isolated from a liver biopsy of a male Caucasian aged 15 years) were obtained from the American Type Culture Collection (ATCC). The chemicals used were: Dimethyl sulfoxide (DMSO), crystal violet and trypan blue dye, purchased from Sigma, St. Louis, Mo., USA; DMEM, RPMI-1640, FBS, HEPES buffer solution, L-glutamine, gentamycin and 0.25% Trypsin-EDTA, purchased from BioWhittaker®, Lonza, Belgium; and Crystal violet stain (1%), composed of 0.5% (w/v) crystal violet and 50% methanol, made up to volume with ddH20 and filtered through a Whatmann No. I filter paper.

In the cytotoxicity assay, the cells were propagated in Dulbecco's modified Eagle's medium (DMEM) supplemented with 10% heat-inactivated fetal bovine serum, 1% L-glutamine, HEPES buffer and 50 µg/ml gentamycin. All cells were maintained at 37° C. in a humidified atmosphere with 5% C0$_2$ and were subcultured two times a week.

Cell toxicity was monitored by determining the effect of the test samples on cell morphology and cell viability.

Cytotoxicity Evaluation Using Viability Assay:

For cytotoxicity assay, the cells were seeded in a 96-well plate at a cell concentration of 1×104 cells per well in 100 µl of growth medium. Fresh medium containing different concentrations of the test sample was added after 24 hours following seeding. Serial two-fold dilutions of the tested chemical compound were added to confluent cell monolayers dispensed into 96-well, flat-bottomed microtiter plates (Falcon, N.J., USA) using a multichannel pipette. The microtiter plates were incubated at 37° C. in a humidified incubator with 5% C0$_2$ for a period of 48 hours. Three wells were used for each concentration of the test sample. Control cells were incubated without test sample and with or without DMSO. The little percentage of DMSO present in the wells (maximal 0.1%) was found not to affect the experiment. After incubation of the cells for 24 hours at 37° C., various concentrations of sample (50, 25, 12.5, 6.25, 3.125 & 1.56 µg) were added, and the incubation was continued for 48 hours and viable cells yield was determined by a colorimetric method.

In brief, after the end of the incubation period, media were aspirated and the crystal violet solution (1%) was added to each well for at least 30 minutes. The stain was removed and the plates were rinsed using tap water until all excess stain was removed. Glacial acetic acid (30%) was then added to all wells and mixed thoroughly and then the absorbance of the plates was measured after being gently shaken on a Microplate reader (TECAN, Inc.), using a test wavelength of 490 nm. All results were corrected for background absorbance detected in wells without added stain. Treated samples were compared with the cell control in the absence of the tested compounds. All experiments were carried out in triplicate.

The cell cytotoxic effect of each tested compound was calculated according to the rapid colorimetric assay for cellular growth and survival: application to proliferation and cytotoxicity assay, published by T. Mosmann in the Journal of Immunology Methods, 1983, 65:55-63; and the antiviral activity of medicinal plants of Nilgriris, published by P. Vijayan et al. in the Indian Journal of Medical Research, 2004, 120: 24-29.

FIG. 26 and table 2 highlight the effectiveness of the reference compound (Doxorubicin) as an inhibitor to the growth and proliferation of liver cancer cells (HepG2) at different concentration degrees.

TABLE 2

| Sample conc. (µg) | Viability % |
|---|---|
| 50 | 10.95 |
| 25 | 14.29 |
| 12.5 | 16.90 |
| 6.25 | 21.03 |
| 3.125 | 30.32 |
| 1.56 | 48.25 |

TABLE 2-continued

| Sample conc. (μg) | Viability % |
|---|---|
| 0.78 | 57.44 |
| 0 | 100.00 |

As illustrated in FIG. 26 and Table 2, the inhibitory activity of doxorubicin standard against HepG2 (Hepatocellular carcinoma cells) as detected under the experimental conditions of the invention showed $IC_{50}=1.2$ μg.

FIG. 27 and table 3 highlight the effectiveness of the compound of the invention, "2-((4-Nitrophenyl)amino)-7,8,9,10-tetrahydrocyclohepta[4,5]thieno[2,3-d][1,3,4]thiadiazolo[3,2-a]pyrimidin-11(6H)-one" as an inhibiter to the growth and proliferation of liver cancer-cells (HepG2) at different concentration degrees.

TABLE 3

| Sample conc. (μg) | Viability % | |
|---|---|---|
| 50 | 3.79 | ✲ |
| 25 | 7.52 | ✲ |
| 12.5 | 10.04 | ✲ |
| 6.25 | 13.92 | ✲ |
| 3.125 | 23.17 | ✲ |
| 1.56 | 32.86 | ✲ |
| 0.78 | 45.74 | ✲ |
| 0.39 | 64.21 | |
| 0 | 100.00 | |

As illustrated in FIG. 27 and Table 3, the inhibitory activity of the compound of the invention against HepG2 (Hepatocellular carcinoma cells) as detected under the experimental conditions of the invention showed $IC_{50}=0.7$ μg.

While particular embodiments of the invention have been illustrated and described in detail herein, it should be understood that various changes and modifications may be made in the invention without departing from the spirit and intent of the invention as defined by the appended claims.

What is claimed is:

1. A chemical compound for inhibiting the growth and proliferation of human liver cancer cells HepG2, said compound consisting of 2-((4-nitrophenyl)amino)-7,8,9,10-tetrahydrocyclohepta[4,5]thieno[2,3-d][1,3,4]thiadiazolo[3,2-a]pyrimidin-11(6H)-one, said compound also being represented as follows:

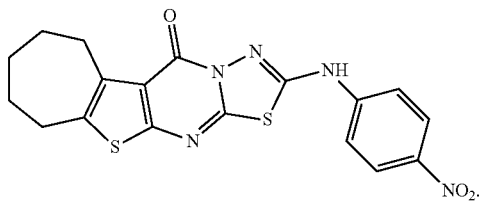 [SMILES: O=c1c2c3c(sc2nc2sc(Nc4ccc([N+](=O)[O-])cc4)nn12)CCCCC3]

2. A method of synthesizing a chemical compound that inhibits the growth and proliferation of human liver cancer cells HepG2, comprising the steps of:
    preparing a first chemical compound expressed by the formula ethyl-2-amino-5,6,7,8-tetrahydro-4H-cyclohepta[b]thiophene-3-carboxylate;
    preparing a second chemical compound by heating of the first chemical compound with hydrazine hydrate in absolute ethanol as solvent, wherein the second compound is expressed by the formula 2-amino-5,6,7,8-tetrahydro-4H-cyclohepta[b]thiophene-3-carbohydrazide;
    preparing a third chemical compound by heating the second chemical compound with carbon disulfide in pyridine as solvent, wherein the third compound is expressed by the formula 3-amino-2-thioxo-2,3,6,7,8,9-hexahydro-1H-cyclohepta[4,5]thieno[2,3-d]pyrimidin-4(5H)-one; and
    preparing a fourth chemical compound by reacting the third chemical compound with 4-nitrophenylisothiocyanate in dimethylformamide as solvent, wherein said fourth chemical compound is expressed by the formula 2-((4-nitrophenyl)amino)-7,8,9,10-tetrahydrocyclohepta[4,5]thieno[2,3-d][1,3,4]thiadiazolo[3,2-a]pyrimidin-11(6H)-one.

3. The method as claimed in claim 2, wherein the second compound is prepared by the steps of:
    a) mixing 1 mmol of the first compound with 5 mmol of hydrazine hydrate and 20 ml of absolute ethanol;
    b) refluxing the mixture for 18 hours to obtain a reaction mixture;
    c) cooling the reaction mixture to separate a precipitate;
    d) filtering the separated precipitate from the mixture to obtain a solid product; and
    e) recrystallizing the solid second compound from hexane.

4. The method as claimed in claim 2, wherein the second compound is prepared by the steps of:
    a) mixing 1 mmol of the first compound with 1 ml of hydrazine hydrate and 2 drops of absolute ethanol;
    b) irradiating the mixture with 390 watts of microwave radiation for 30 minutes to produce a reaction mixture;
    c) cooling the reaction mixture to separate a precipitate;
    d) filtering the separated precipitate from the mixture to obtain a solid product; and
    e) recrystallizing the solid second compound from hexane.

5. The method as claimed in claim 2, wherein the second compound is prepared by the steps of:
    a) mixing 1 mmol of the first compound with 5 mmol of hydrazine hydrate and 10 ml of absolute ethanol;
    b) irradiating the mixture with ultrasound for 4 hours to produce a reaction mixture;
    c) cooling the reaction mixture to separate a precipitate;
    d) filtering the separated precipitate from the mixture to obtain a solid product; and
    e) recrystallizing the solid second compound from hexane.

6. The method as claimed in claim 3, wherein the third compound is prepared by the steps of:
    a) mixing 1 mmol of the second compound with 20 ml of pyridine and 5 mmol of carbon disulfide;
    b) refluxing the mixture in a water bath for 21 hours to produce a reaction mixture;
    c) cooling the reaction mixture to separate a precipitate;
    d) filtering the separated precipitate from the mixture to obtain a solid product; and
    e) washing the solid third compound with methanol.

7. The method as claimed in claim 3, wherein the third compound is prepared by the steps of:
    a) mixing 1 mmol of the second compound with 10 ml of pyridine and 5 mmol of carbon disulfide;
    b) irradiating the mixture with ultrasound for 8 hours to produce a reaction mixture;
    c) cooling the reaction mixture to separate a precipitate;

d) filtering the separated precipitate from the mixture to obtain a solid product; and
e) washing the solid third compound with methanol.

8. The method as claimed in claim 4, wherein the third compound is prepared by the steps of:
   a) mixing 1 mmol of the second compound with 20 ml of pyridine and 5 mmol of carbon disulfide;
   b) refluxing the mixture in a water bath for 21 hours to obtain a reaction mixture;
   c) cooling the reaction mixture to separate a precipitate;
   d) filtering the separated precipitate from the mixture to obtain a solid product; and
   e) washing the solid third compound with methanol.

9. The method as claimed in claim 4, wherein the third compound is prepared by the steps of:
   a) mixing 1 mmol of the second compound with 10 ml of pyridine and 5 mmol of carbon disulfide;
   b) irradiating the mixture with ultrasound for 8 hours to obtain a reaction mixture;
   c) cooling the reaction mixture to separate a precipitate;
   d) filtering the separated precipitate from the mixture to obtain a solid product; and
   e) washing the solid third compound with methanol.

10. The method as claimed in claim 5, wherein the third compound is prepared by the steps of:
    a) mixing 1 mmol of the second compound with 20 ml of pyridine and 5 mmol of carbon disulfide;
    b) refluxing the mixture in a water bath for 21 hours to obtain a reaction mixture;
    c) cooling the reaction mixture to separate a precipitate;
    d) filtering the separated precipitate from the mixture to obtain a solid product; and
    e) washing the solid third compound with methanol.

11. The method as claimed in claim 5, wherein the third compound is prepared by the steps of:
    a) mixing 1 mmol of the second compound with 10 ml of pyridine and 5 mmol of carbon disulfide;
    b) irradiating the mixture with ultrasound for 8 hours to obtain a reaction mixture;
    c) cooling the reaction mixture to separate a precipitate;
    d) filtering the separated precipitate from the mixture to obtain a solid product; and
    e) washing the solid third compound with methanol.

12. The method as claimed in claim 6, wherein the fourth compound is prepared by the steps of:
    a) mixing 1 mmol of the third compound with 2 mmol of 4-nitrophenylisothiocyanate and 20 ml of dimethylformamide;
    b) refluxing the mixture for 10 hours to obtain a reaction mixture;
    c) cooling the reaction mixture to separate a precipitate;
    d) filtering the separated precipitate out of the mixture to obtain a solid product;
    e) washing the solid product with water;
    f) drying the solid product; and
    g) recrystallizing the solid fourth compound from hexane.

13. The method as claimed in claim 6, wherein the fourth compound is prepared by the steps of:
    a) mixing 1 mmol of the third compound with 2 mmol of 4-nitrophenylisothiocynate and 2 ml of dimethylformamide;
    b) irradiating the mixture with 520 watts of microwave energy for 2 minutes to obtain a reaction mixture;
    c) cooling the reaction mixture to separate a precipitate;
    d) filtering the separated precipitate out of the mixture to obtain a solid product;
    e) washing the solid product with water;
    f) drying the solid product; and
    g) recrystallizing the solid fourth compound from hexane.

14. The method as claimed in claim 6, wherein the fourth compound is prepared by the steps of:
    a) mixing 1 mmol of the third compound with 10 ml of dimethylformamide and 2 mmol of 4-nitrophenylisothiocyanate;
    b) irradiating the mixture with ultrasound for 4 hours to obtain a reaction mixture;
    c) cooling the reaction mixture to separate a precipitate;
    d) filtering the separated precipitate out of the mixture to obtain a solid product;
    e) washing the solid product with water;
    f) drying the solid product; and
    g) recrystallizing the solid fourth compound from hexane.

15. The method as claimed in claim 7, wherein the fourth compound is prepared by the steps of:
    a) mixing 1 mmol of the third compound with 2 mmol of 4-nitrophenylisothiocyanate and 20 ml of dimethylformamide;
    b) refluxing the mixture for 10 hours to obtain a reaction mixture;
    c) cooling the reaction mixture to separate a precipitate;
    d) filtering the separated precipitate out of the mixture to obtain a solid product;
    e) washing the solid product with water;
    f) drying the solid product; and
    g) recrystallizing the solid fourth compound from hexane.

16. The method as claimed in claim 7, wherein the fourth compound is prepared by the steps of:
    a) mixing 1 mmol of the third compound with 2 mmol of 4-nitrophenylisothiocyanate and 2 ml of dimethylformamide;
    b) irradiating the mixture with 520 watts of microwave energy for 2 minutes to obtain a reaction mixture;
    c) cooling the reaction mixture to separate a precipitate;
    d) filtering the separated precipitate out of the mixture to obtain a solid product;
    e) washing the solid product with water;
    f) drying the solid product; and
    g) recrystallizing the solid fourth compound from hexane.

17. The method as claimed in claim 7, wherein the fourth compound is prepared by the steps of:
    a) mixing 1 mmol of the third compound with 10 ml of dimethylformamide and 2 mmol of 4-nitrophenylisothiocyanate;
    b) irradiating the mixture with ultrasound for 4 hours to obtain a reaction mixture;
    c) cooling the reaction mixture to separate a precipitate;
    d) filtering the separated precipitate out of the mixture to obtain a solid product;
    e) washing the solid product with water;
    f) drying the solid product; and
    g) recrystallizing the solid fourth compound from hexane.

18. The method as claimed in claim 8, wherein the fourth compound is prepared by the steps of:
    a) mixing 1 mmol of the third compound with 2 mmol of 4-nitrophenylisothiocyanate and 20 ml of dimethylformamide;
    b) refluxing the mixture for 10 hours to obtain a reaction mixture;
    c) cooling the reaction mixture to separate a precipitate;
    d) filtering the separated precipitate out of the mixture to obtain a solid product;
    e) washing the solid product with water;
    f) drying the solid product; and
    g) recrystallizing the solid fourth compound from hexane.

19. The method as claimed in claim 8, wherein the fourth compound is prepared by the steps of:
   a) mixing 1 mmol of the third compound with 2 mmol of 4-nitrophenylisothiocyanate and 2 ml of dimethylformamide;
   b) irradiating the mixture with 520 watts of microwave energy for 2 minutes to obtain a reaction mixture;
   c) cooling the reaction mixture to separate a precipitate;
   d) filtering the separated precipitate out of the mixture to obtain a solid product;
   e) washing the solid product with water;
   f) drying the solid product; and
   g) recrystallizing the solid fourth compound from hexane.

20. The method as claimed in claim 8, wherein the fourth compound is prepared by the steps of:
   a) mixing 1 mmol of the third compound with 10 ml of dimethylformamide and 2 mmol of 4-nitrophenylisothiocyanate;
   b) irradiating the mixture with ultrasound for 4 hours to obtain a reaction mixture;
   c) cooling the reaction mixture to separate a precipitate;
   d) filtering the separated precipitate out of the reaction mixture to obtain a solid product;
   e) washing the solid product with water;
   f) drying the solid product; and
   g) recrystallizing the solid fourth compound from hexane.

21. The method as claimed in claim 9, wherein the fourth compound is prepared by the steps of:
   a) mixing 1 mmol of the third compound with 2 mmol of 4-nitrophenylisothiocyanate and 20 ml of dimethylformamide;
   b) refluxing the mixture for 10 hours to obtain a reaction mixture;
   c) cooling the reaction mixture to separate a precipitate;
   d) filtering the separated precipitate out of the mixture to obtain a solid product;
   e) washing the solid product with water;
   f) drying the solid product; and
   g) recrystallizing the solid fourth compound from hexane.

22. The method as claimed in claim 9, wherein the fourth compound is prepared by the steps of:
   a) mixing 1 mmol of the third compound with 2 mmol of 4-nitrophenylisothiocyanate and 2 ml of dimethylformamide;
   b) irradiating the mixture with 520 watts of microwave energy for 2 minutes to obtain a reaction mixture;
   c) cooling the reaction mixture to separate a precipitate;
   d) filtering the separated precipitate from the mixture to obtain a solid product;
   e) washing the solid product with water;
   f) drying the solid product; and
   g) recrystallizing the solid fourth compound from hexane.

23. The method as claimed in claim 9, wherein the fourth compound is prepared by the steps of:
   a) mixing 1 mmol of the third compound with 10 ml of dimethylformamide and 2 mmol of 4-nitrophenylisothiocyanate;
   b) irradiating the mixture with ultrasound for 4 hours to obtain a reaction mixture;
   c) cooling the reaction mixture to separate a precipitate;
   d) filtering the separated precipitate from the mixture to obtain a solid product;
   e) washing the solid product with water;
   f) drying the solid product; and
   g) recrystallizing the solid fourth compound from hexane.

24. The method as claimed in claim 10, wherein the fourth compound is prepared by the steps of:
   a) mixing 1 mmol of the third compound with 2 mmol of 4-nitrophenylisothiocyanate and 20 ml of dimethylformamide;
   b) refluxing the mixture for 10 hours to obtain a reaction mixture;
   c) cooling the reaction mixture to separate a precipitate;
   d) filtering the separated precipitate from the mixture to obtain a solid product;
   e) washing the solid product with water;
   f) drying the solid product; and
   g) recrystallizing the solid fourth compound from hexane.

25. The method as claimed in claim 10, wherein the fourth compound is prepared by the steps of:
   a) mixing 1 mmol of the third compound with 2 mmol of 4-nitrophenylisothiocyanate and 2 ml of dimethylformamide;
   b) irradiating the mixture with 520 watts of microwave energy for 2 minutes to obtain a reaction mixture;
   c) cooling the mixture to separate a precipitate;
   d) filtering the separated precipitate from the mixture to obtain a solid product;
   e) washing the solid product with water;
   f) drying the solid product; and
   g) recrystallizing the solid fourth compound from hexane.

26. The method as claimed in claim 10, wherein the fourth compound is prepared by the steps of:
   a) mixing 1 mmol of the third compound with 10 ml of dimethylformamide and 2 mmol of 4-nitrophenylisothiocyanate;
   b) irradiating the mixture with ultrasound for 4 hours to obtain a reaction mixture;
   c) cooling the reaction mixture to separate a precipitate;
   d) filtering the separated precipitate from the mixture to obtain a solid product;
   e) washing the solid product with water;
   f) drying the solid product; and
   g) recrystallizing the solid fourth compound from hexane.

27. The method as claimed in claim 11, wherein the fourth compound is prepared by the steps of:
   a) mixing 2 mmol of 4-nitrophenylisothiocyanate with 1 mmol of the third compound and 20 ml of dimethylformamide;
   b) refluxing the mixture for 10 hours to obtain a reaction mixture;
   c) cooling the reaction mixture to separate a precipitate;
   d) filtering the separated precipitate from the mixture to obtain a solid product;
   e) washing the solid product with water;
   f) drying the solid product; and
   g) recrystallizing the solid fourth compound from hexane.

28. The method as claimed in claim 11, wherein the fourth compound is prepared by the steps of:
   a) mixing 1 mmol of the third compound with 2 mmol of 4-nitrophenylisothiocyanate and 2 ml of dimethylformamide;
   b) irradiating the mixture with 520 watts of microwave energy for 2 minutes to obtain a reaction mixture;
   c) cooling the reaction mixture to separate a precipitate;
   d) filtering the separated precipitate from the mixture to obtain a solid product;
   e) washing the solid product with water;
   f) drying the solid product; and
   g) recrystallizing the solid fourth compound from hexane.

29. The method as claimed in claim 11, wherein the fourth compound is prepared by the steps of:

a) mixing 1 mmol of the third compound in 10 ml of dimethylformamide and 2 mmol of 4-nitrophenylisothiocyanate;
b) irradiating the mixture with ultrasound for 4 hours to obtain a reaction mixture;
c) cooling the reaction mixture to separate a precipitate;
d) filtering the separated precipitate out of the mixture to obtain a solid product;
e) washing the solid product with water;
f) drying the solid product; and
g) recrystallizing the solid fourth compound from hexane.

30. The method as claimed in claim 2, wherein the first compound is prepared by the steps of:
a) stirring together cycloheptanone, ethylcyanoacetate, sulfur and ethanol;
b) adding diethylamine until the sulfur is dissolved;
c) after the sulfur is dissolved, stirring the mixture of cycloheptanone, ethyl cyanoacetate, sulfur, ethanol and diethylamine overnight at room temperature to obtain a reaction mixture;
d) cooling the reaction mixture to separate a precipitate;
e) filtering the separated precipitate from the mixture to obtain a solid first product;
f) drying the solid first product; and
g) recrystallizing the solid first product with petroleum ether.

31. The method as claimed in claim 30, wherein:
in step a) 0.05 mmol of the cycloheptanone, 0.05 mmol of the ethylcyanoacetate, 1.67 g of the sulfur, and 10 ml of the ethanol are stirred together, and in step b) 10 ml of the diethylamine is added dropwise until the sulfur is dissolved.

32. A method of synthesizing a chemical compound that is effective to inhibit the growth and proliferation of human liver cancer cells HepG2, comprising the steps of:
preparing a first compound from a reaction mixture consisting of cycloheptanone, ethylcyanoacetate, sulfur, ethanol and diethylamine, wherein the first compound is expressed by the formula ethyl-2-amino-5,6,7,8-tetrahydro-4H-cyclohepta[b]thiophene-3-carboxylate;
preparing a second compound by heating of the first compound with hydrazine hydrate in absolute ethanol as solvent, wherein the second compound is expressed by the formula 2-amino-5,6,7,8-tetrahydro-4H-cyclohepta[b]thiophene-3-carbohydrazide;
preparing a third compound by heating the second compound with carbon disulfide in pyridine as solvent, wherein the third compound is expressed by the formula 3-amino-2-thioxo-2,3,6,7,8,9-hexahydro-1H-cyclohepta[4,5]thieno[2,3-d]pyrimidin-4(5H)-one; and
reacting the third compound with 4-nitrophenylisothiocyanate in dimethylformamide as solvent to produce the chemical compound that is effective to inhibit the growth and proliferation of human liver cancer cells HepG2, said compound being expressed by the formula 2-((4-nitrophenyl)amino)-7,8,9,10-tetrahydrocyclohepta[4,5]thieno[2,3 d][1,3,4]thiadiazolo[3,2-a]pyrimidin-11(6H)-one.

* * * * *

UNITED STATES PATENT AND TRADEMARK OFFICE
CERTIFICATE OF CORRECTION

PATENT NO.       : 9,447,119 B2
APPLICATION NO.  : 14/593683
DATED            : September 20, 2016
INVENTOR(S)      : Zainab Saeed Alghamdi It is certified that error appears in the above-identified patent and that said Letters Patent is hereby corrected as shown below:

On the Title Page

Item (54) at the top of Column 1, and in the Specification, Column 1, Lines 1-4:
The title should be changed from "CHEMICAL COMPOUND FOR INHIBITING THE GROWTH AND PROLIFERATION OF HUMAN LIVER CANCER CELLS HEPG2 AND METHOD FOR SYNTHESIZING IT" to --A CHEMICAL COMPOUND FOR INHIBITING THE GROWTH AND PROLIFERATION OF HUMAN LIVER CANCER CELLS HEPG2 AND METHOD FOR SYNTHESIZING IT--.

Item (57) in the Abstract:
Line 2, "tetrahydro cyclohepta" should read --tetrahydrocyclohepta--;
Line 17, "disulphide" should be --disulfide--;
Line 19, "N,N-methylformamide" should read --N,N-dimethylformamide--.

In the Drawings

Please replace Fig. 1-27 with Fig. 1-27 as shown on the attached pages.

In the Specification

Column 2:
Line 29, that portion of the chemical name reading "*tetrahydro[1]benzothieno*" should read --*tetrahydro[1]benzothieno*--;
Lines 38 and 39, "2004; 13; 347. 2004; 13; 347" should read --2004; 13; 347--.

Column 3:
Lines 11-14, the text beginning with "second, preparing" in Line 11 and ending with "compound I" in Line 14 should be replaced with --second, preparing a second chemical compound by heating of the first chemical compound (I) with hydrazine hydrate in ethanol as solvent.--;
Line 16, "disulphide" should be --disulfide--.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*

Column 5:
Line 61, "3222.50 cm-1" should read --3222.50 cm$^{-1}$--.

Column 6:
Lines 14 and 15, "disulphide", each occurrence, should read --disulfide--;
Line 45, "[M$^{+], 203}$ (19.4)" should read --[M$^+$], 203 (19.4)--;
Lines 53 and 54, "4-nitrophenyl isothiocyanate" should read --4-nitrophenylisothiocyanate--;
Line 54, "N,N-dimethyl formamide" should read --N,N-dimethylformamide--;
Line 58, "4-nitro phenyl isothiocyanate" should read --4-nitrophenylisothiocyanate--;
Line 66, "4-nitrophenylisothio cyanate" should read --4-nitrophenyisothiocyanate--.

Column 7:
Line 20, "14024.34" should read --1402.34--.

Column 8:
Line 14, "1×104" should read --1×10$^4$--.